United States Patent
Blume et al.

(10) Patent No.: US 9,845,552 B2
(45) Date of Patent: Dec. 19, 2017

(54) SET MEMBERSHIP TESTERS FOR ALIGNING NUCLEIC ACID SAMPLES

(71) Applicant: Verinata Health, Inc., Redwood City, CA (US)

(72) Inventors: Erich D. Blume, Millbrae, CA (US); John P. Burke, Reno, NV (US); Hui Huang, Sunnyvale, CA (US)

(73) Assignee: Verinata Health, Inc., San Diego, CA (US)

( * ) Notice: Subject to any disclaimer, the term of this patent is extended or adjusted under 35 U.S.C. 154(b) by 0 days.

(21) Appl. No.: 14/354,528

(22) PCT Filed: Oct. 18, 2012

(86) PCT No.: PCT/US2012/060892
§ 371 (c)(1),
(2) Date: Apr. 25, 2014

(87) PCT Pub. No.: WO2013/062856
PCT Pub. Date: May 2, 2013

(65) Prior Publication Data
US 2014/0274752 A1   Sep. 18, 2014

Related U.S. Application Data

(60) Provisional application No. 61/552,374, filed on Oct. 27, 2011.

(51) Int. Cl.
*G06F 19/22* (2011.01)
*C40B 30/02* (2006.01)

(52) U.S. Cl.
CPC .............. *C40B 30/02* (2013.01); *G06F 19/22* (2013.01)

(58) Field of Classification Search
None
See application file for complete search history.

(56) References Cited

U.S. PATENT DOCUMENTS

2007/0067108 A1   3/2007   Buhler et al.
2007/0202525 A1   8/2007   Quake et al.
(Continued)

OTHER PUBLICATIONS

M Ehrich, C Deciu, T Zwiefelhofer, JA Tynan, L Cagasan, R Tim, V Lu, R McCullough, E McCarthy, AOH Nygren, J Dean, et al. Noninvasive detection of fetal trisomy 21 by sequencing of DNA in maternal blood: a study in a clincal setting. American Journal of Obstetrics and Gynecology. Mar. 2011, 204, 205.e1-11.*

(Continued)

*Primary Examiner* — John S. Brusca
*Assistant Examiner* — Olivia M Wise
(74) *Attorney, Agent, or Firm* — Weaver Austin Villeneuve & Sampson LLP

(57) ABSTRACT

Disclosed are methods and tools for rapidly aligning reads to a reference sequence. These methods and tools employ Bloom filters or similar set membership testers to perform the alignment. The reads may be short sequences of nucleic acids or other biological molecules and the reference sequences may be sequences of genomes, chromosomes, etc. The Bloom filters include a collection of hash functions, a bit array, and associated logic for applying reads to the filter. Each filter, and there may be multiple of these used in a particular application, is used to determine whether an applied read is present in a reference sequence. Each Bloom filter is associated with a single reference sequence such as the sequence of a particular chromosome. In one example, chromosomal abundance is determined by aligning reads from a sequencer to multiple chromosomes, each having an associated Bloom filter or other set membership tester.

21 Claims, 11 Drawing Sheets

(56) References Cited

U.S. PATENT DOCUMENTS

| | | | |
|---|---|---|---|
| 2009/0029377 A1 | 1/2009 | Lo et al. | |
| 2010/0112590 A1 | 5/2010 | Lo et al. | |
| 2010/0138165 A1 | 6/2010 | Fan et al. | |
| 2011/0201507 A1 | 8/2011 | Rava et al. | |
| 2011/0245085 A1* | 10/2011 | Rava | C12Q 1/6806 506/2 |
| 2011/0257889 A1 | 10/2011 | Klammer et al. | |
| 2012/0100548 A1 | 4/2012 | Rava et al. | |
| 2012/0264115 A1 | 10/2012 | Rava | |

OTHER PUBLICATIONS

P Melsted and JK Pritchard. Efficient counting of k-mers in DNA sequences using a bloom filter. BMC Bioinformatics, 2011, vol. 12, p. 333.*

LW Hillier, GT Marth, AR Quinlan, D Dooling, G Fewell, D Barnett, P Fox, JI Glasscock, M Hickenbotham, W Huang, VJ Magrini, RJ Richt, SN Sander, DA Stewart, M Stromberg, EF Tsung, T Wylie, T Schedl, RK Wilson, ER Mardis. Whole-genome sequencing and variant discovery in C. elegans. Nature Methods, 2008, vol. 5, No. 2, p. 183-188.*

International Search Report and Written Opinion dated Mar. 26, 2013 for PCT Application No. PCT/US2012/060892.

Stranneheim, Henrik et al., "Classification of DNA sequences using Bloom filters," Bioinformatics, vol. 26, No. 13, May 13, 2010, pp. 1595-1600.

Moraru, Iulian et al, "Exact pattern matching with feed-forward Bloom filters," ACM Journal of Experimental Algorithmics, vol. 16, No. 16, Article 2.1, May 2011, pp. 1-19.

"Bloom Filters" from Wikipedia, portion of article available online and obtained from <http://en.wikipedia.org/wiki/Bloom_filters> prior to Oct. 27, 2011, 6 pp.

Examination Report dated Jan. 20, 2015 issued in Australian Application No. 2012327251.

"Casava Software Version 1.6 User Guide" Illumina, Catalog # SY-960-1601, Nov. 2009.

* cited by examiner

SET MEMBERSHIP TESTERS FOR ALIGNING NUCLEIC ACID SAMPLES

CROSS-REFERENCE TO RELATED APPLICATIONS

This application claims the benefit of and priority to U.S. Provisional Application Ser. No. 61/552,374, filed Oct. 27, 2011, the contents of which are incorporated herein by reference in their entirety and for all purposes.

SEQUENCE LISTING

The instant application contains a Sequence Listing which has been submitted electronically in ASCII format and is hereby incorporated by reference in its entirety. Said ASCII copy, created on Apr. 18, 2016, is named ARTEP003_sequence_listing_ST25.txt and is 746 bytes in size.

BACKGROUND

It is often desirable to determine the abundance or relative concentration of particular nucleic acid sequences. Such nucleic acid sequences include, for example, chromosomes, genome sequences, mRNAs, peptides, genotypes, or haplotypes. Various tools for mapping or aligning nucleic acid sequences to a reference sequence are known and used. However the available techniques are often not tailored for the needs of a particular application such as determining chromosomal abundance. For example, the available techniques often provide both relevant and irrelevant information for the application at hand. As a consequence, they may not be optimized for rapidly providing the relevant information.

SUMMARY

Disclosed are methods and tools for rapidly aligning reads to a reference sequence. These methods and tools employ Bloom filters or similar set membership testers to perform the alignment. The reads may be short sequences of nucleic acids or other biological molecules and the reference sequences may be sequences of genomes, chromosomes, etc. The Bloom filters include a collection of hash functions, a bit array, and associated logic for applying reads to the filter. Each filter, and there may be multiple of these used in a particular application, is used to determine whether an applied read is present in a reference sequence. Each Bloom filter is associated with a single reference sequence such as the sequence of a particular chromosome. In one example, chromosomal abundance is determined by aligning reads from a sequencer to multiple chromosomes, each having an associated Bloom filter or other set membership tester.

Certain aspects of this disclosure pertain to methods of aligning nucleic acid sequence reads to a reference sequence, in which the methods are characterized by the following operations: (a) receiving a first read containing the sequence of a first nucleic acid segment from a sample; (b) applying the first read to a Bloom filter to determine whether the first nucleic acid segment is found in a first reference sequence represented by the Bloom filter; (c) receiving a second read containing the sequence of a second nucleic acid segment from the sample; and (d) applying the second read to the Bloom filter to determine whether the second nucleic acid segment is found in the first reference sequence represented by the Bloom filter. In certain embodiments, the method also includes applying the first read to a second Bloom filter to determine whether the first nucleic acid segment is found in a second reference sequence represented by the second Bloom filter.

In certain embodiments, a reference sequence represents a biological sequence such as a nucleic acid or a peptide sequence under consideration. In one example, the first and second reference sequences, which have first and second associated Bloom filters, are sequences of a first chromosome and a second chromosome of an organism. In some embodiments employing two or more Bloom filters for two or more chromosomes, the method may include the following operations: (i) applying a plurality of additional reads from the sample to the Bloom filters, and (ii) determining the number of reads that are found in the first and second chromosomes to assess a relative abundance of the first and second chromosomes in the sample. Such method may be employed to detect a chromosomal aneuploidy from the relative abundance of the first and second chromosomes in the sample. In a specific embodiment, the sample includes a mixture of genomes. For example, the sample may include cells or free DNA taken from a pregnant individual.

In certain embodiments, the Bloom filter has 9 or 10 hash functions. In certain embodiments, the hash functions employ at most about 5 machine instructions per character of a read string. In certain embodiments, the Bloom filter includes a bit array having between about $1.5 \times 10^{10}$ to $8.5 \times 10^{11}$ bit positions. In certain embodiments, the Bloom filter has a false positive probability of at most about 0.00001.

In some embodiments, the methods also involve applying the first read to an exclusion region Bloom filter to determine whether the first read should be excluded from alignment to a reference sequence.

An aspect of the present disclosure concerns methods of generating a tool for aligning nucleic acid sequence reads to a reference sequence, which methods may be characterized by the following operations: (a) receiving a reference sequence of a long nucleic acid; (b) defining multiple slices of the reference sequence, where each slice is short sequence of contiguous base pairs from a unique site on the reference sequence; (c) adding each of the slices to a Bloom filter; and (d) incorporating the Bloom filter into the tool for aligning nucleic acid sequence reads. In certain embodiments, the Bloom filter may have one or more of the properties mentioned above.

In certain embodiments, the reference sequence is a sequence of a first chromosome of an organism. In such embodiments, the method may repeat operations (a)-(d) for a second chromosome of an organism.

In some cases, the methods may further include the following operations: (d) receiving one or more excluded sequences from the chromosome; (e) defining multiple slices of the excluded sequences, where each slice is short sequence of contiguous base pairs from a unique site on the excluded sequences; (f) adding each of the slices from (e) to an exclusion Bloom filter; and (g) incorporating the exclusion Bloom filter into the tool for aligning nucleic acid sequence reads.

Another aspect of the invention pertains to computer program products including machine-readable media on which are stored program instructions for implementing at least some portion of the methods described above. The machine readable media may be tangible and/or non-transitory. Any of the methods disclosed herein may be represented, in whole or in part, as program instructions that can be provided on such computer readable media. In addition, the invention pertains to various combinations of data and associated data structures generated and/or used as described herein.

Another aspect of the disclosure pertains to apparatus for aligning nucleic acid sequence reads to a reference sequence. Such apparatus may include a sequencer that receives a nucleic acid sample and provides reads of nucleic acid sequences from the sample, and a sequence alignment tool including a computer program product as described.

These and other features will be described in more detail below with reference to the associated drawings.

DETAILED DESCRIPTION

Definitions

Figure 1A:
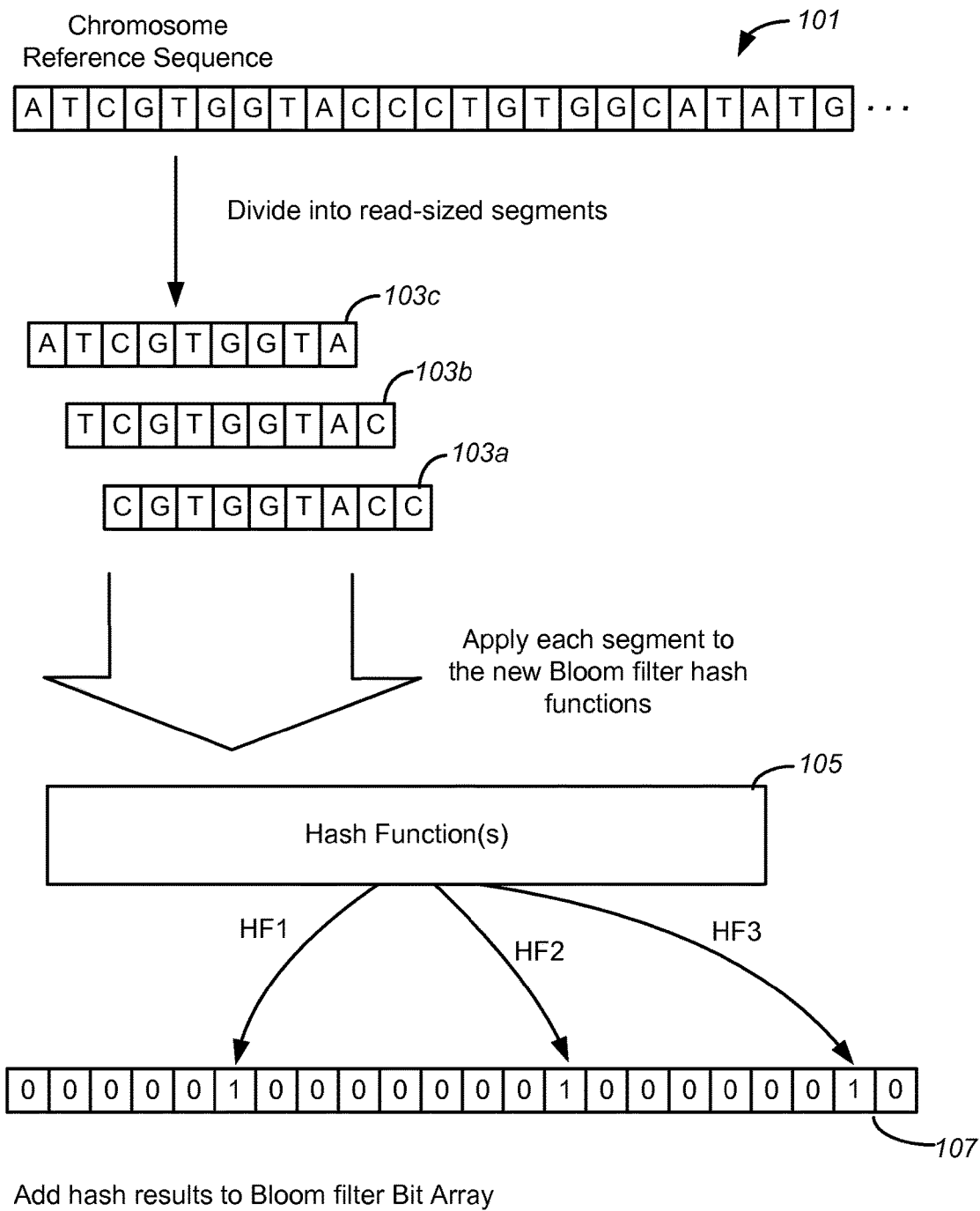
FIG. 1A illustrates the process of creating a Bloom filter from a chromosome reference sequence (SEQ ID NO:1).

The following discussion is provided as an aid in understanding certain aspects and advantages of the disclosed embodiments.

The term "read" refers to a sequence read from a portion of a nucleic acid sample. Typically, though not necessarily, a read represents a short sequence of contiguous base pairs in the sample. The read may be represented symbolically by the base pair sequence (in ATCG or the meta-symbol '.') of the sample portion. It may be stored in a memory device and processed as appropriate to determine whether it matches a reference sequence or meets other criteria. A read may be obtained directly from a sequencing apparatus or indirectly from stored sequence information concerning the sample.

The term "tag" also refers to short sequences from a nucleic acid sample. Typically, a tag contains a read and associated information for that read such as the location of the sequence in the genome. For some purposes, the terms read and tag are interchangeable herein.

Frequently herein "reads" are described as sequences of nucleic acids that are 36 base pairs in length (36mers). Of course, the disclosed embodiments are not limited to this size. Smaller and larger reads are suitable in many applications. For applications that align reads to the human genome, a read of size 30 base pairs or greater is generally considered sufficient to map a sample to a single chromosome. Much larger tags/reads are suitable for some applications. With whole genome sequencing, reads on the order of 1000 base pairs or greater may be used. In certain embodiments, a read may have a length of between about 20 and 10,000 base pairs, or between about 30 and 1000 base pairs, or between about 30 and 50 base pairs.

A "reference sequence" is a sequence of a biological molecule, which is frequently a nucleic acid sequence such as a chromosome or genome. Typically multiple reads are members of a given reference sequence. In certain embodiments, a read is compared to a reference sequence to determine whether the reference sequence contains the read sequence. This process is sometimes referred to as alignment.

In various embodiments, the reference sequence is significantly larger than the reads that are aligned to it. For example, it may be at least about 100 times larger, or at least about 1000 times larger, or at least about 10,000 times larger, or at least about $10^5$ times larger, or at least about $10^6$ times larger, or at least about $10^7$ times larger.

In one example, the reference sequence is that of a full length human genome. Such sequences may be referred to as genomic reference sequences. In another example, the reference sequence is limited to a specific human chromosome such as chromosome 13. Such sequences may be referred to as chromosome reference sequences. Other examples of reference sequences include genomes of other species, as well as chromosomes, sub-chromosomal regions (such as strands), etc. of any species.

In certain embodiments, portions of the reference sequence may be excluded, in some cases intentionally, in the construction of a Bloom filter or other alignment tool. For example, it may be desirable to remove regions of the referenced sequence that are deemed uninteresting such as regions of long repeated sequences, etc.

In various embodiments, the reference sequence is a consensus sequence or other combination derived from multiple individuals. However, in certain applications, the reference sequence may be taken from a particular individual.

The term "alignment" refers to the process of comparing a read to a reference sequence and thereby determining whether the reference sequence contains the read sequence. If the reference sequence contains the read, the read may be mapped to the reference sequence or, in certain embodiments, to a particular location in the reference sequence. In some cases, alignment simply tells whether or not a read is a member of a particular reference sequence (i.e., whether the read is present or absent in the reference sequence). For example, the alignment of a read to the reference sequence for human chromosome 13 will tell whether the read is present in the reference sequence for chromosome 13. A tool that provides this information may be called a set membership tester. In some cases, an alignment additionally indicates a location in the reference sequence where the read maps to. For example, if the reference sequence is the whole human genome sequence, an alignment may indicate that a read is present on chromosome 13, and may further indicate that the read is on a particular strand of chromosome 13. In various embodiments, the information provided by alignment is sufficient for determining the chromosomal abundance of a sample.

A "site" is a unique position in a reference sequence corresponding to a read or tag. In certain embodiments, it specifies the identity of a chromosome (e.g., chromosome 13), a strand of the chromosome, and an exact position in the chromosome.

A "Bloom filter" is set membership tester used to determine whether a string or other input is a member of a reference sequence or other set. It typically comprises data and associated testing algorithms for determining set membership. In some embodiments, the only input required for membership testing is a string such as a read.

In certain embodiments described herein, the Bloom filter is used to determine whether a read is found in a reference sequence such as a chromosome reference sequence or a genomic reference sequence.

Two operations can be performed on Bloom filters: test and add. In certain embodiments, add operations are used to construct Bloom filters from sequence slices of a reference sequence, and test operations are used to align reads to the reference sequence. A "slice" is a read-sized sequence taken from a site in the reference sequence.

A "bit array" is one component of a Bloom filter. It is an array of 1s and 0s and is typically stored in memory. In various embodiments, a single Bloom filter is provided for a defined location in a reference sequence (e.g., a single Bloom filter is provided for a particular chromosome in a genome). Initially, prior to adding any slices to a bit array, all positions in the array contain 0s. As a Bloom filter bit array is populated with bits corresponding to sequence slices from sites in the reference sequence, specific positions in the bit array are changed from 0 to 1.

During testing, reads provided to the filter are converted to a pattern of 1s associated with positions in the bit array. This pattern can be compared to the existing Bloom filter to determine membership. If the pattern is present in the bit array, there is a probability that tag is present in the location associated with the Bloom filter. If the pattern is not present in the array, the tag is not present in the location.

The term "hash function" is given its conventional meaning herein. Of relevance to this disclosure, hash functions are components of Bloom filters. String hash functions are of particular interest. Certain properties of suitable hash functions will be presented below.

A "sample" contains a nucleic acid having one or more segments to be aligned or otherwise tested against a reference sequence. The sample can comprise a bodily fluid from a subject, e.g., blood, plasma, serum, sputum, saliva, urine, excrement, pus, lymph, mucous or the like. For example, the subject can be pregnant and the sample can be a plasma sample.

The subject providing a sample to be tested can be an organism comprising polynucleotide sequences, e.g., a plant, an insect such as a fly, or an animal. In some embodiments, the subject is a mammal, e.g., a mouse, rat, dog, monkey or human. The subject may be known to have a particular condition, such as a particular disorder. In some cases, the subject might be an individual with a disease such as a cancer, or might be infected with a foreign body such as a microorganism, e.g., a virus. In some cases, the subject can be a pregnant individual.

In some embodiments, the suspect is suspected but not confirmed to have the disorder. The methods can be used in the diagnosis of the disorder. In an exemplary embodiment, the methods of the invention are used to determine an amount of tumor DNA circulating in the blood of a subject diagnosed with a proliferative disorder.

In various embodiments, the sample includes polynucleotide sequences which are detected by sequencing or other form of assaying. The polynucleotide sequences can be deoxyribonucleic acid (DNA) polynucleotide sequences, both naturally occurring and/or synthetic sequences. In other embodiments, the polynucleotide sequences comprise ribonucleic acid (RNA), e.g., mRNA, tRNA, siRNA, small RNAs, micro RNAs or the like. The sequences may have non-naturally occurring nucleic acid building blocks, e.g., nucleotides that have chemical modifications not typically found in nature. Nucleotides include without limitation pyrimidines comprising cytosine (C), thymine (T), and uracil (U), and purines comprising adenine (A) and guanine (G).

In some examples, the sample is a maternal plasma sample containing a mixture of maternal and fetal cell free DNA. The cell free DNA may be sequenced and the resulting reads may be aligned to chromosomes. Chromosomal abundance information can be obtained and used to determine the presence or absence of fetal aneuploidy.

INTRODUCTION AND OVERVIEW

Many applications require efficient alignment of reads to reference sequences. Some such applications detect a trait under consideration (e.g., the ploidy of particular human chromosomes). In some cases, the alignment permits detection of aberrations such as aneuploidy. In various embodiments employing alignment techniques disclosed herein, each of many reads generated from a sample is aligned to one of multiple chromosomes of interest (e.g., the 23 human chromosomes) to generate a number of mapped reads for each such chromosome. This allows detection of trisomy 21, for example. Methods for determining fetal aneuploidy by generation and mapping of sequence tags have been previously described (Fan et al., PNAS 105:16266-16271 (2008); Chiu et al. PNAS 105:20458-20463 (2008); Chiu et al., BMJ 2011; 342:c7401 (2011); US Patent Publication Nos. 2007/0202525 filed Feb. 2, 2007, 2010/0138165 filed Jan. 29, 2010, 2009/0029377 filed Jul. 23, 2008, 2010/0112590 filed Nov. 6, 2009; and pending U.S. patent application Ser. No. 12/958,352 filed Dec. 1, 2010, Ser. No. 12/958,353 filed Dec. 1, 2010, Ser. No. 13/087,842 filed Apr. 15, 2011, and Ser. No. 13/191,366 filed Jul. 26, 2011, each incorporated herein by reference).

Another application concerns aligning reads to specific alleles in a polymorphism. Such aligning may be used to determine, for example, the fractions of nucleic acid from two or more different individuals in a single sample. In a specific example, the alignment is used to determine the fraction of fetal DNA in the free DNA in the bloodstream of a pregnant female. Methods for performing this determination are presented in U.S. Provisional Patent Application 61/474,362, filed Apr. 12, 2011, which is incorporated herein by reference in its entirety.

Generally, the alignment methods disclosed herein may be employed in any application for determining variations in the number of copies of any one or more nucleic acid sequence (CNV), and/or variations in the sequence(s) i.e. polymorphisms. Copy number variants/variations include deletions, including microdeletions, insertions, including microinsertions, duplications, multiplications, inversions, translocations and complex multi-site variants. CNV encompass complete chromosomal aneuploidies and partial chromosomal aneuplodies. Polymorphisms encompass sequence differences that include single nucleotide polymorphisms (SNPs), tandem SNPs, small-scale multi-base deletions or insertions, called IN-DELS (also called deletion insertion polymorphisms or DIPs), Multi-Nucleotide Polymorphisms (MNPs), Short Tandem Repeats (STRs), restriction fragment length polymorphism (RFLP), and polymorphisms comprising any other change of sequence in a chromosome. Differences in genomic sequences include combinations of polymorphisms. For example, polymorphisms can encompass the combination of one or more SNPs and one or more STR. Polymorphisms can be indicative, informative, or both. For example, indicative polymorphisms indicate the presence of fetal cell-free DNA in a maternal sample. Informative polymorphisms yield information about the fetus—for example, the presence or absence of a disorder, abnormality, or any other biological information such as the stage of gestation or gender.

Typically, in conventional alignment techniques, DNA samples are processed by genomic analysis machines. A DNA sample is input and then analyzed to identify stretches of consecutive base pairs that form the reads. A computer then performs alignment in an attempt to determine where in the genome (or other reference sequence) the reads are located.

Certain embodiments disclosed herein align reads to reference sequences in a computationally efficient manner. Some conventional techniques can take hours to days or weeks to align all reads from a human genomic sample to some or all of the 23 chromosomes, depending on the number of reads produced. This can be a significant bottleneck in characterizing a sample. It results from, primarily, the number of memory accesses required to align each read.

In some applications, the alignment involves reading tens of millions to hundreds of millions of short reads. It is not uncommon for a sample of human DNA to produce 30 million to 100 million 36mer reads per sample. Soon billions of reads may be routinely produced from a single sample. In some implementations employing Bloom filters as disclosed herein, alignment may achieve speeds on the order of milliseconds per read, or on the order of a few minutes (e.g., 10 to 60 minutes) to map a whole DNA genomic sample to the human genome.

A complication in alignment arises because the human genome is highly repetitive. There are some 36mers that appear millions of times across the genome. In theory there are a few petabytes of possible 36mers in a human genomic reference sequence, but due to the size of the human genome and the fact that a large fraction of the genome is highly repetitive, only a small fraction of this petabyte scale sequence space actually appears in the human genome. Thus, the range of possible reads is highly condensed. Further, for various applications such as some chromosomal abundance measurements, the highly repetitive portions of the genome are not relevant.

Conventional aligners often employ indexes containing tree structures, which have nodes and edges. To use an index, the algorithm seeking to align a read traverses the tree using the read sequence as input. At a leaf node of the tree, there is a pointer to the location in the reference sequence (e.g., a particular chromosome).

One conventional aligner, bowtie, employs a technique in which the entire reference sequence is compressed to a very large suffix tree structure which is compressed to reduce memory footprint. Individual reads are matched to regions of the reference sequence by applying them to the tree and traversing over the nodes of the tree to obtain an unambiguous match or alignment. During alignment, bowtie uses each read to traverse the index, accessing memory multiple times as it does so.

In an alternative to the conventional tree approach (but nevertheless another aligner), the index is constructed from all the various reads generated from a sample of human DNA. The reference genome is then scanned, and alignments are generated by searching the index for the portion of the genome currently being scanned. It has been found that this approach may require a day or more to align a single sample to the human genome. Additionally (and also contributing to the long alignment time), this method generally has very large memory requirements.

A significant challenge encountered when using indexes is that the process requires many memory look ups for a single alignment. In various implementations, the alignment process implemented with an index requires at least twelve look ups to perform alignment of a single 36mer. It is not unusual for an optimized aligner to require an hour or more to align a complete human genome sample. It would be desirable to complete the task much faster, e.g., on the order of 30 minutes or less or 15 minutes or less.

Bloom Filters in Alignment

In accordance with various embodiments, Bloom Filters are used to align reads to a reference sequence. More generally, Bloom filters may be used to test arbitrary sequences to determine membership in a region of a reference sequence. Such Bloom filter tools may wholly or partially replace a conventional index-type aligner.

Bloom filters are a type of set membership tester. In certain embodiments, their only inputs are the sequence strings of reads (e.g., the sequences of 36mers). Generally, Bloom filters contain (1) "k" different hash functions for converting reads to hash values, and (2) an array or other data structure for recording the hashes from a reference sequence and for testing reads during alignments. In some implementations, the array stores hashes as bits at particular locations in the array determined by the hash values. Thus, for example, an array may store a single bit per hash at a single array position defined by the hash value. Additionally, the alignment tool may include (3) logic for testing reads against Bloom filters for reference sequences (sometimes called "test" functionality), and optionally (4) logic for creating Bloom filters from reference sequences (sometimes called "add" functionality).

Bloom filters are sometimes said to have "add" and "test" functionality. Both functions return only "true" or "false". Both functions operate on a Bloom Filter and take a read as an argument. For both functions, if the read was already present in the Bloom Filter when the function is called, the function will return "true" and otherwise will return "false". In addition to this functionality, the "add" function will also add the read to the Bloom Filter if it was not already present. In some cases, the "add" function does not return any value at all, usually due to implementation concerns.

FIG. 1A depicts an example process in which a chromosome reference sequence is used to create a Bloom filter for chromosome alignment. As depicted, a chromosome reference sequence 101 is provided as a character string of nucleotide bases. The string is divided into read-sized segments or "slices" 103a, 103b, 103c, etc. Each of these slices has the same number of characters as present in reads generated from samples which will be analyzed using the Bloom filter. As shown, each of the slices 103 is derived from a contiguous sequence of nucleotides in the chromosome reference sequence 101. Further, each one of these slices 103 has a sequence which is offset by one base from the preceding slice taken from the reference. More generally, a series of slices is created, typically one for each position in the reference sequence to be represented by the Bloom filter. For a chromosome, a Bloom filter may be created by dividing the reference chromosome into all possible overlapping reads.

As shown in FIG. 1A, each of these segments 103 is applied to the one or more hash functions of the new Bloom filter. It is assumed that the hash functions have been previously selected. In the figure, these hash functions are depicted as a block 105. When one of the slices is presented to the hash functions, the functions will each output a distinct value which represents a position in a bit array 107.

A bit or other indicator is inserted at each such position. In some embodiments, the bit array initially contains all zeros. In a specific embodiment, the hash value output defines an offset into the array.

The example of FIG. 1A assumes that there are three hash functions in the Bloom filter. As a consequence, the figure shows slices 103a giving rise to three outputs (HF1, HF2, and HF3), each populating a position in the Bloom filter bit array 107. Of course, typically there will be many slices used to populate the Bloom filter, each giving rise to three outputs. Also, in certain embodiments, there will be more or fewer hash functions the three indicated in FIG. 1A.

Assuming there are three hash functions in block 105, each slice will result in three separate bits inserted into the array. During testing, the same three hash functions are applied to the read being tested. The Bloom filter test logic determines whether 1s exist at each of the positions associated with the values calculated by the hash functions. Note that each hash function may produce a very different output value for the same input. Further, the hash function outputs may be bounded by modulus arithmetic to conform to the size of the bit array.

Figure 1B:
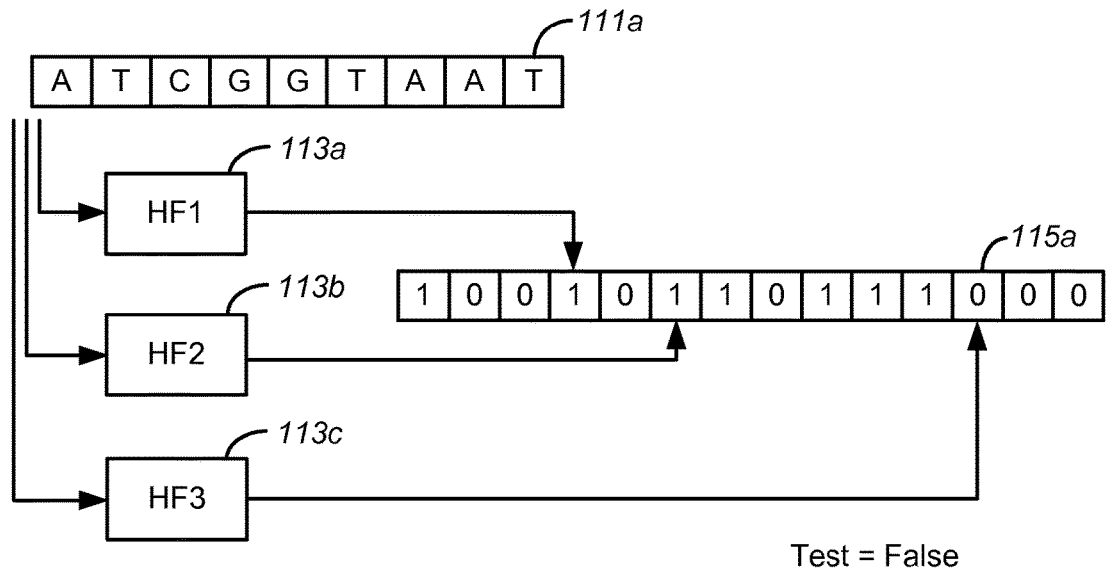
FIG. 1B illustrates the process of testing reads against a Bloom filter.
Figure 1B:
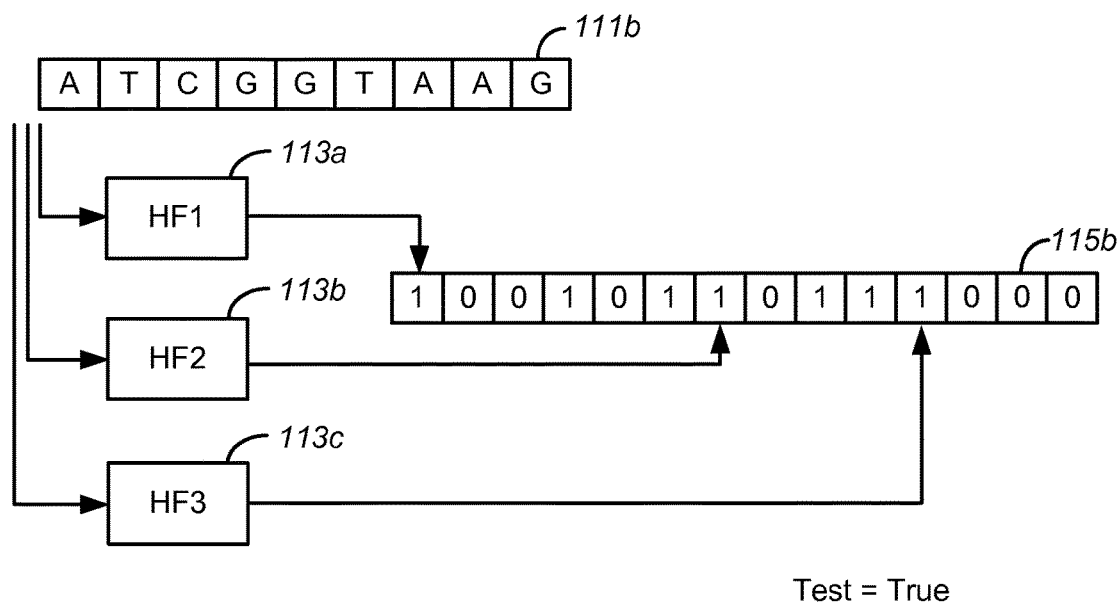

FIG. 1B depicts an alignment phase, in which a Bloom filter is used to align reads from a sample into chromosomes. In the depicted embodiment, two separate reads 111a and 111b have sequences that differ by a base at a single position. The Bloom filter includes three hash functions 113a, 113b, and 113c, along with a bit array 115. During a test, read 111a is fed to each of the three hash functions which each calculate their own output. As explained, these output values may be interpreted as offsets into bit array 115. As shown in the depicted embodiment, read 111a is tested and produces a false result. This is because the bit position identified by the output offset position of hash function 113c contains a 0 rather than a 1. It does not matter that the other two hash functions produce outputs identifying bit array positions having values of 1. In the case of read 111b, the test produces a true result. This is because each of the three hash functions hashing read 111b gives an output pointing to a position having a 1 value.

There are certain advantages to using Bloom filters for aligning reads to reference sequences. For example, Bloom filters do not provide false negatives, and to the extent that they provide false positives, these do so at a pre-set level dictated by the design of the Bloom filter. Therefore, the filter can be constructed to meet a false positive rate that is acceptable for a given application.

Further, Bloom filters are able to very rapidly test whether a read aligns in a reference sequence or portion that reference sequence. In certain embodiments, a Bloom filter requires about 10 or fewer memory accesses to align a 36 base pair tag. In some cases, the filter requires only 9 or fewer memory accesses for such alignment. In many conventional computer systems this translates total align time of a fraction of a millisecond or less per read.

Additionally, the code for implementing Bloom filters is small and portable. In certain embodiments, only about 50 lines or less is needed to fully code the algorithm implementing the core 'add' and 'test' functions.

Still further, alignment of many reads can be performed in parallel. There are multiple ways of parallelizing the alignment analysis. In one approach, the alignment algorithm provides a single read to each of multiple separate Bloom filters and thereby conducts multiple membership tests in parallel. For example, a read can be tested for membership in multiple chromosomes, each having its own Bloom filter. Additionally, a read can be tested in parallel for membership in a One Read Filter or a Multiple Read Filter for a given chromosome. (These filters will be described below.) Separately, multiple processes may load all the Bloom filters together so they show up in memory only once and perform look ups for a single read sequence against those Bloom filters at one time.

While the embodiments are described in terms of Bloom filters, it should be understood that generally other set membership testers may be used in place of Bloom filters, and the disclosed embodiments are not limited to a particular Bloom filter structure unless specifically stated. Thus, the concept of a Bloom filter as applied to the embodiments described herein is not strictly limited to the conventional understanding of a Bloom filter. For example, the embodiments disclosed herein impose no limitations on size of bit arrays, numbers of hash functions, types of hash functions, acceptable false positive rates. Further, data structures other than bit arrays may be employed to hold the hash value information generated from slices during creation of Bloom filters.

Designing Bloom Filters

The size of the bit array and the number of hash functions can be specified by first setting the capacity of the Bloom filter and the acceptable limits of false positives. The capacity is reflected by the size of the bit array. If the number and types of hash functions is fixed, then increasing the capacity of the filter reduces percentage of false positives. Generally, the capacity of the Bloom filter increases approximately linearly with decreasing percentage of false positive results. Further, the capacity of the filter can be increased while preserving the look up speed (e.g., to about 9 memory look ups or less).

As explained all Bloom filters have a defined false positive rate. This rate represents the probability that the filter will respond to a test with "true" when in fact the read is not actually present in the associated reference sequence. Acceptable levels of false positives (also referred to as "sensitivity") may be set for a given application. In some embodiments, an acceptable theoretical probability of false positives for setting a Bloom filter to align reads to a reference sequence (e.g., sequences of chromosomes in the human genome) is about 0.0001 or less, or about 0.00005 or less or about 0.00001 or less. In a further specific embodiment, the probability of false positives is about 0.000005 or less or about 0.000001 or less.

It should be understood that the theoretical and observed false positive rates do not always match. In some contexts, for example, the observed false positive rate is about 10 times greater than the theoretical rate. This may be due to repetition in the genome and repetition in the input to the Bloom filter. As a consequence, a given read, which may cause a false positive, will show up dozens of times.

Hash functions used in Bloom filters should be well behaved functions. In certain embodiments, they meet the following two criteria: (1) they are fast at string hashing, and (2) they have a good avalanche probability.

The speed of a hash function may be characterized by various parameters including the number of machine instructions required to hash a character. In certain embodiments, it will be desirable to use hash functions requiring about 2-5 machine instructions per character. To this end, some hash functions are written in machine instructions. For example, the functions may be machine coded in a digital signal processor or similar architecture.

Because processors execute instructions in various orders, the number of instructions/character is not a definitive measure of a hash function's speed. Therefore an empirical evaluation is often appropriate. It has been found that suitably fast hash functions for certain implementations described herein operate at speeds of about 6 instructions per character or faster. One example of a hash function operating at this speed is Murmur3.

To improve the overall speed at which a Bloom filter tests reads, the aligning system may be designed such that the multiple hash functions of the Bloom filter execute in parallel. In other words, the filter may be constructed so that two more of the hash functions hash the same read in parallel. In one implementation, the logic for doing this is hard coded in a processor such as a DSP programmed onto a programmable logic device or an ASIC. In such designs, a register may be employed for holding the read string and permitting effectively simultaneous access by two or more (e.g., all) of the hash functions. In some implementations, the code or other logic associated with a Bloom filter may be written to cache or otherwise remember some of the more recent hashes (e.g., the most recent 400).

It should be understood that a string contains multiple characters, so hashing a string will require that each character (or possibly each group of characters) is processed separately. Effectively, the hash function loops over each character. In one embodiment, a 36 character read sequence is treated as a 36 character string, in which each character (A, T, C, and G) is represented by an 8 bit word (e.g., as an ASCII character). The characters are treated by the string hash in sequence, while accumulating the result from each successive character iteration. In some embodiments, the final hash value is a 32 bit word. As mentioned, the hash value may be treated as an offset into the Bloom filter bit array. In some embodiments, the input string is compressed prior to hashing.

A good avalanche probability in a hash function is evident when an input is changed slightly (by, for example, flipping a single bit) and the output changes significantly. For example, each bit in the output has a significant probability of switching value. Simply stated, two very similar input strings produce two very different outputs.

A hash function with a perfect avalanche probability is one in which a change of 1 bit in the input produces an output in which there is a 50% probability of a change in each and every bit in the output. In certain embodiments, hash functions employed in a Bloom filter have avalanche probabilities in the range of about 0.48 and above. Thus, for example, a change in any one bit of a 256 bit input produces an output in which each and every bit of a 32 bit word has at least a 48% chance of changing from its previous output value. Effectively, a large fraction of the output bit positions will be toggled.

As explained, a Bloom filter includes a plurality of hash functions. In certain embodiments, all filters include at least 5 hash functions, and in some cases the filters include about 7 to 15 hash functions. In a specific embodiment, a Bloom filter has 9 or 10 hash functions.

Each of the hash functions in the Bloom filter should be different. In some cases, this means providing intrinsically different hash functions. However, this is not always required. For example, some Bloom filters may use a single function that takes a read sequence and another value (e.g., an integer) as an input. Some or all of the different hash functions employed in the Bloom filter use this single function but with different second value inputs.

Examples of hash functions that have been found suitable are the following: Murmur 3 Hash, Fowler-Noll-Vo hash, and Jenkins hash.

The number of hash functions "k" has a functional dependence on the false positive probability only when the bit array size is appropriately chosen. The size or "capacity" of a bit array is represented by the character "n" and represents the number of inserts that can be made in a Bloom filter. Intuitively it can be seen that if one continues adding values to a Bloom filter's bit array, the fraction of slots occupied by 1s increases (at some point all slots will have 1s) and probability of false positives also goes up. Thus, a capacity "n" should be set based on an expected number of reads that can be input to a Bloom filter. In the example of a Bloom filter intended to represent all 36mer reads of a human chromosome, n would be the number of bases in that chromosome, which might range between about 250 million and 40 million, which is the number of expected unique read sequences in the chromosome. If one chooses a bit array capacity and also chooses a false positive probability, p, then the minimum bit array size (number of bits in the array), m, may is given as follows:

$$m = -n(\ln(p))/(\ln(2))^2$$

Similarly, the number of hash functions may be specified as follows:

$$k = m/n \ln(2)$$

In some cases (e.g., those involving chromosome alignment), the value of m may be, for example, about $1.5 \times 10^{10}$ to $8.5 \times 10^{11}$ (200 megabytes to 10 gigabytes per filter) In some cases, the value of m is about $4 \times 10^{10}$ to $8 \times 10^{10}$ (500 megabytes to 1 gigabyte per filter).

Regarding performance, a Bloom filter and associated processing logic may require on the order of milliseconds per read, or on the order of a few minutes (e.g., about 10 to 15 minutes) to align an entire sample to the human genome. For example, the per read speed may be about 1 ms or less, or about 0.5 ms or less, or about 0.1 ms or less. Generally, the number of memory look ups associated with a read is constant regardless of the size of the read, although the time to compute the hash function will increase linearly as the size of the reads increase.

In a typical index based aligner, the alignment processing involves reading in the string, permuting and compressing the string, and traversing the tree. In some cases, the alignment further includes seeding the index with a portion of the string and then extending to the full string length. For comparison, the operations required with a Bloom filter are frequently more streamlined. For example, alignment may require only the following operations: Read string in, hash it X times, and determine whether bits exist at the hash locations in memory.

The memory footprint for a Bloom filter may be similar to or slightly larger than the footprint for an index tree such as those employed in competing methods. In certain embodiments, the memory required for a Bloom filter representing a human genome (including all 23 human chromosomes with Multiple Read Filters) is about 1-50 gigabytes or in some cases about 10-40 gigabytes.

Generally, a Bloom filter will indicate whether there is an exact match between a read sequence and a site on the reference sequence. An exact match can be important when it is necessary to determine unambiguously that a particular tag aligns exactly with one and only one chromosome. In some embodiments, the aligner supports mismatches. In other words, the aligner can manage to align reads even if they are inexact. Mismatch support may be a desirable feature (though optionally disabled until needed). Sample reads are often not in 100% agreement with the consensus genome due to genetic differences. Inexact matches may allow a read to be accurately (or inaccurately) mapped to the location it belongs (or does not belong) to even if it has a small number of 'errors' from the reference genome.

Bloom Filter Aligner Architecture

As illustrated in FIGS. 1A and B, aligning using Bloom filters may be conducted in a two phase procedure. Initially, multiple Bloom filters are produced, one for each location of interest in the reference sequence (e.g., one for each chromosome in a genome). The resulting Bloom filters are then used repeatedly for testing reads on the fly from various samples. This however need not be the case, as it is possible to construct Bloom filters during alignment of test samples. For example, an index-type aligner may be employed to analyze samples and determine membership in chromosomes. When the aligner establishes that a read from a sample aligns to a particular chromosome that read is added to a Bloom filter for the chromosome. In this manner, Bloom filters are gradually populated with reads that are aligned using a separate alignment tool.

In embodiments where the complete set of Bloom filters is produced prior to aligning samples, each Bloom filter may be produced by dividing an associated chromosome reference sequence into all possible slice sequences. See the example of FIG. 1A. For example if a read sequence is 36 base pairs in length, the number of slices used in producing the Bloom filter will be equal to the length of the chromosome minus 36.

More generally, the Bloom filters are produced by dividing the entire relevant portion of the reference sequence into distinct slices which are then used to construct the individual Bloom filters. One Bloom filter is created for each location of interest; for example, one Bloom filter for each chromosome in the human genome. The individual slices used to populate a Bloom filter for any given location are taken as each possible contiguous sequence of nucleotides in the reference sequence that fit within the read size. These sequences overlap with one another. As mentioned, a typical read size is 36 base pairs. Thus, as an example, if a location of the reference sequence contains 100 million nucleotides, that location will be divided into 100 million less 36 separate slices to populate the Bloom filter for that location. As explained above, the populating is performed by using the add function of the Bloom filter. During an alignment phase of this first implementation employing Bloom filters, reads taken from a sample are applied to Bloom filters for each of the various locations, e.g., each of the chromosomes.

In certain embodiments, multiple Bloom filters may be created for one or more of the chromosomes (or other locations) under consideration. For example, one filter may be used to validly align read sequences to particular chromosomes (in the manner explained above) and a separate additional filter may be used to mark the read as special (for either the chromosome under consideration or for the entire genome). For example, the second filter may provide additional valuable information; e.g., that a given read occurs more than once in a chromosome or it is part of an excluded region of the chromosome.

In certain embodiments, Bloom filters are designed to identify read sequences that should be automatically discarded, regardless of whether they align to any particular chromosome or other location under consideration. To this end, special Bloom filters may be employed to identify "invalid" or unusable read sequences. Such sequences are not, in certain applications, permitted to align to any chromosome. Portions of a reference sequence that are deemed invalid may be used to create one or more of these specialized Bloom filters.

In certain embodiments, one or more exclusion regions of the chromosomes or other reference sequence are identified for exclusion. These regions are then used to create one or more special exclusion Bloom filters. Any read sequences aligning to such regions are excluded from alignment to any chromosome.

When an exclusion region is known and identified within the chromosome, that region is simply excluded from membership in the Bloom filter for the chromosome. Thus, if the Bloom filter designer determines that there is an exclusion region for the chromosome, the designer excludes slices from that region when creating the Bloom filter for the chromosome under consideration. In other embodiments, a Bloom filter is constructed from slices within an exclusion region or multiple exclusion regions. In one implementation, an exclusion region Bloom filter is created for each location (e.g., for each chromosome). Thus, each chromosome may contain both an "alignment Bloom filter" and an "exclusion region Bloom filter". Exclusion regions may be excluded for a variety of reasons. For example, some regions of the genome are highly repetitive. Chromosome Y contains vast regions of repeating sequences.

In certain embodiments, the set membership tester is designed to indicate not only whether a read is present in the chromosome (or other reference sequence) under consideration but also whether it is present more than once. One way to implement this is by creating a second Bloom filter that identifies slices that appear more than once in the reference sequence. When the membership tester is being created, each new slice is tested against a first filter. If it is not already present in that filter, then it is added. If, however, it is found to be already present in the filter, it is added to a second filter, which filter includes only those slices that occur more than once in the reference sequence.

In certain embodiments, a read aligning to a chromosome more than once is not considered in classifying a sample. Such embodiments might involve chromosomal abundance measurements such as are used in aneuploidy detection methods. In alternative embodiments, reads that align to a given chromosome more than once are also used to classify the sample.

In certain embodiments, the entire reference sequence for an associated chromosome or other location is used to produce a "One Read Filter." This filter may include sequences from an excluded region and/or sequences that occur more than once in a chromosome. This is only one of many possible implementations that employ separate exclusion and alignment filters. In certain embodiments, a "Multiple Read Filter" includes sequences from exclusion regions as well as sequences that occur more than once in a chromosome or other reference sequence.

In some implementations, for any given read produced during a sample analysis, the alignment logic applies it to every Bloom filter at every location. In a certain embodiments, this means that the read sequence is applied each separate Bloom filter for each of 23 human chromosomes under consideration.

During this process, if a "true" is returned in reply to a test of the read under consideration to any of the Bloom filters under consideration, then the read is considered to align to the chromosome. However, this is not the end of the process. The read is separately applied to each other Bloom filter. If, after testing the read against each Bloom filter, the read aligns to only one chromosome Bloom filter, then that alignment is deemed to be valid and the alignment is used in the information charactering the sample. If, however, the read aligns to more than one Bloom filter, none of the alignments is considered valid and the read sequence is discarded from further consideration. Alignment to more than one Bloom filter may result from a false positive, or possibly because the read is found on more than one chromosome. Regardless of the source of the multiple alignments, such data may not be sufficiently useful for certain applications such as detection of aneuploidy, particularly when the sample data is available in great abundance, as it is in high throughput genomic sequencing.

In alternative embodiments, alignment information is not necessarily discarded when a read aligns to more than one chromosome. This may be the case when, for example, studying whether a sample sequence from one species is found in the genome of a different species. Also, when the application provides relatively little data, such as in a gene expression study (which produces considerably less data than studies on the underlying genomic DNA), it may be desirable conserve the limited available data and therefore not discard reads that alignment to multiple locations.

In various embodiments, when a read aligns with a second Bloom filter (assuming one is used in the embodiment being implemented), that read is discarded from all further consideration, regardless of whether it aligns to any one or more chromosomes in the alignment Bloom filters of the reference sequence. In certain embodiments, the alignment operation is terminated for a given read as soon as the read aligns to any of the second Bloom filters.

FIGS. 2A through 2D depict testing of a read against a series of Bloom filters organized into Chromosome Membership Objects, where there is one Chromosome Membership Object for each chromosome of a genomic reference sequence. In each of the figures, a read 121 is applied against each of four Chromosome Membership Objects 123, 125, 127, and 129. Each of these objects is associated with a separate chromosome of the genomic reference sequence. For example, Chromosome Membership Object 123 is associated with chromosome 1. This means that the Bloom filters contained in this object were generated from a chromosome reference sequence for chromosome 1.

Each of the Chromosome Membership Objects includes two separate Bloom filters, one populated by all the slices of the associated chromosome reference sequence that are not part of an exclusion region, and the other populated by only slices that are found to occur more than once with in the associated chromosome reference sequence and with sequences taken from the exclusion region. As explained, the first of these Bloom filters is referred to as a One Read Filter (see filters 131a through d) and second is referred to as a Multiple Read Filter (see filters 133a through d). Note that a Chromosome Membership Object is but one example of a Reference Membership Object, which may allow testing for alignment to any of many different reference sequences, such as whole genomic reference sequences, chromosome strand reference sequences, etc.

Figure 2A:
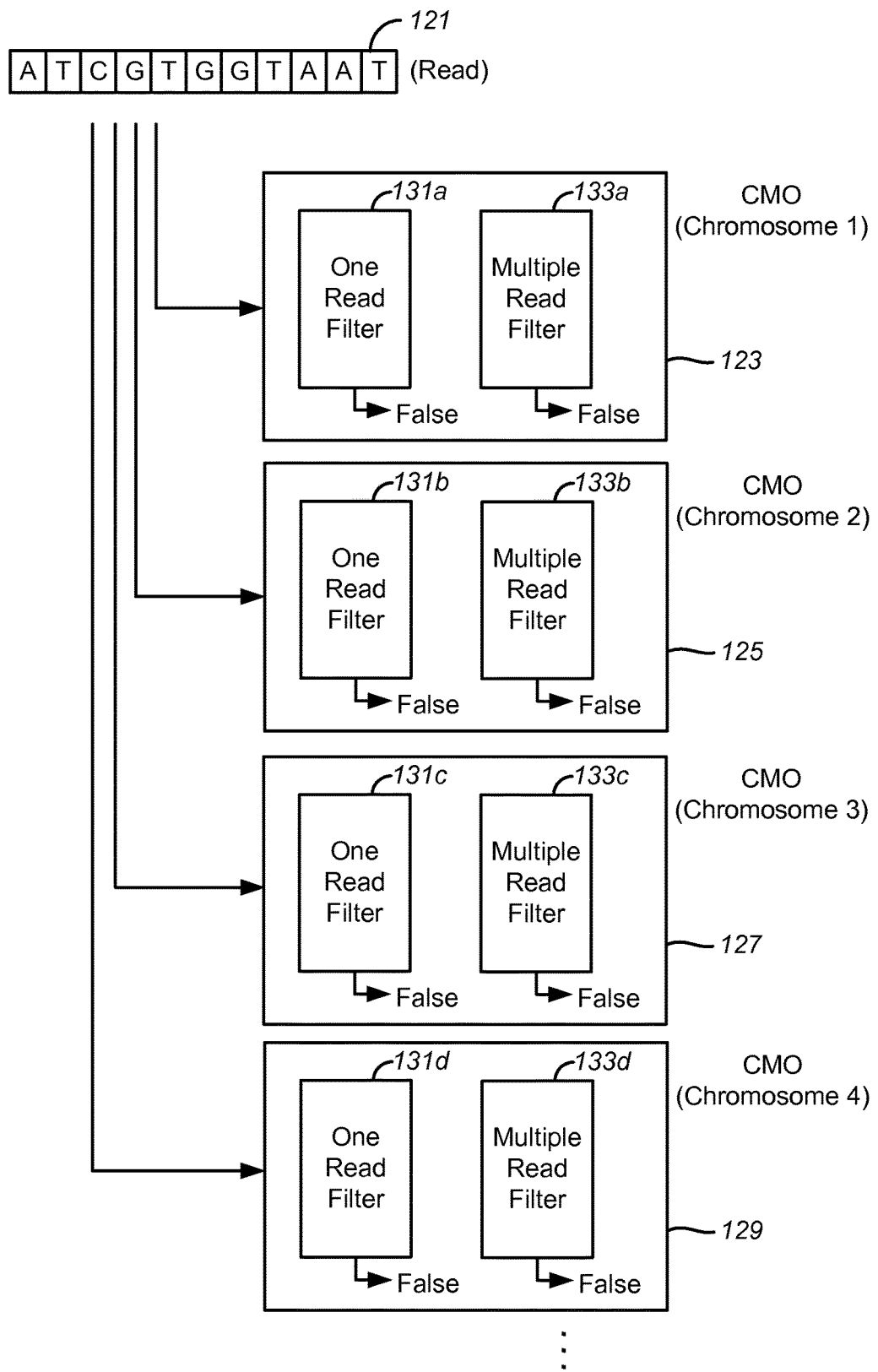
FIGS. 2A-D show testing a read sequence (SEQ ID NO:2) against four chromosome alignment objects.
Figure 2B:
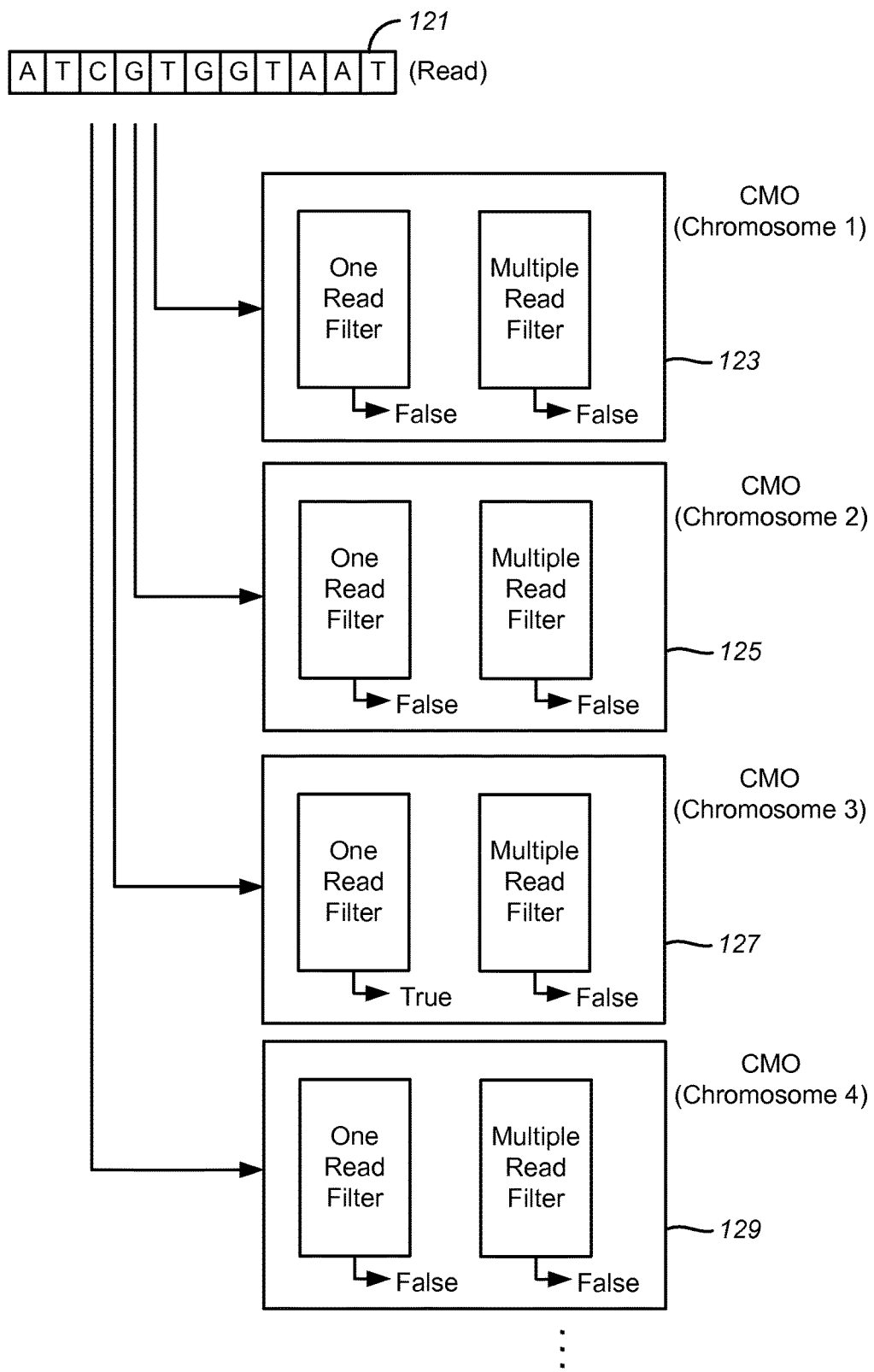

In the example depicted in FIG. 2A, a valid alignment of read 121 is not found. This is because testing read 121 against each of the One Read Filters, 131a-d, produces false results. In the example depicted in FIG. 2B, by contrast, the read 121 does produce a valid alignment because one and only one of the One Read Filters produces a result of true upon testing. See Chromosome Membership Object 127. Further, none of the Multiple Read Filters in the example of FIG. 2B produces a true result on testing. As a consequence, the alignment to chromosome 3 is deemed valid.

Figure 2C:
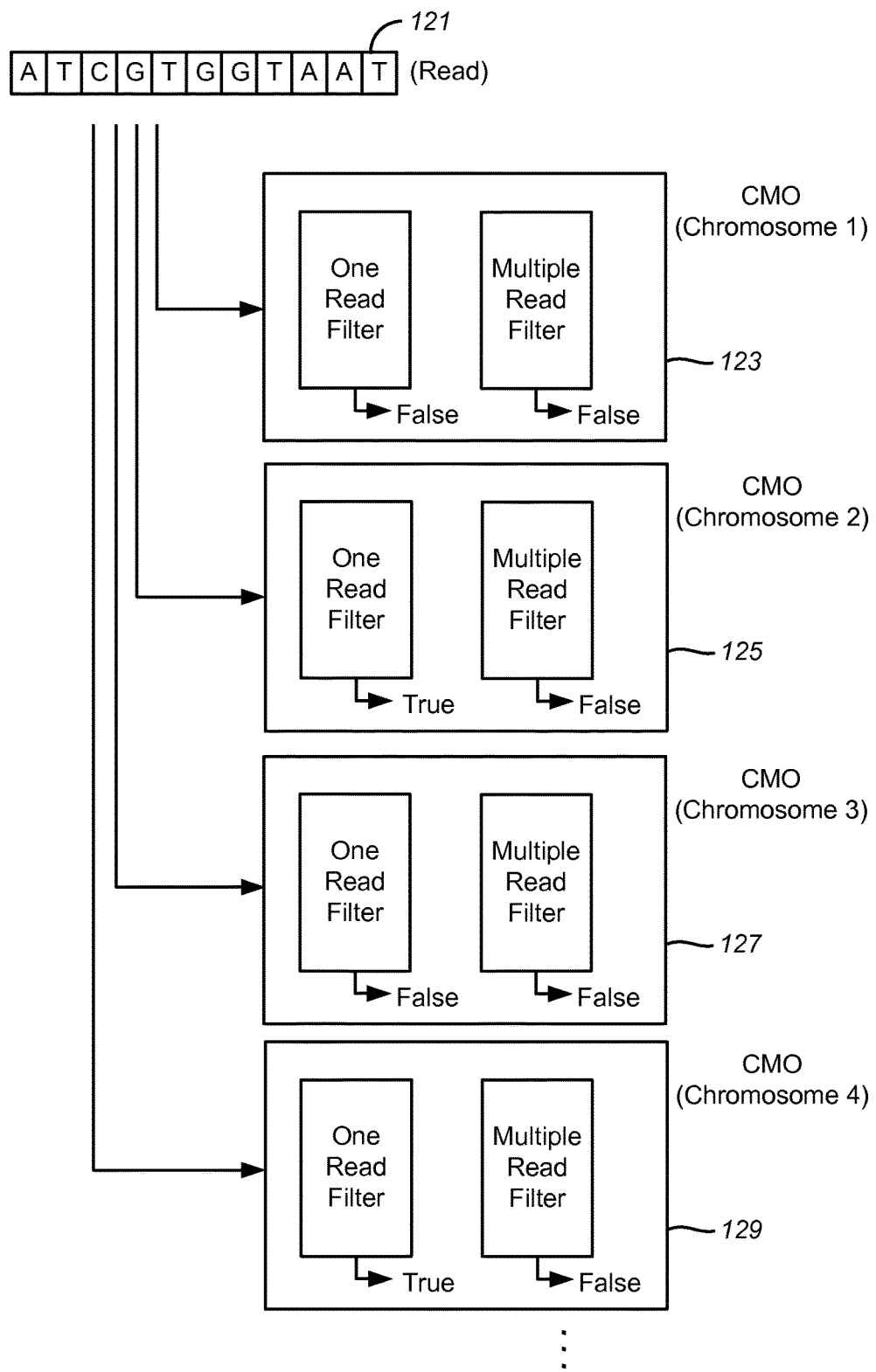

In the example shown in FIG. 2C an invalid alignment occurs because the read 121 aligns to both chromosomes 2 and 4. Note that the One Read Filter in the associated Chromosome Membership Objects for these chromosomes each returns a true in response to the test. An invalid alignment would similarly result if the read produces a true not only for two distinct One Read Filters but also to any one or more Multiple Read Filters.

Figure 2D:
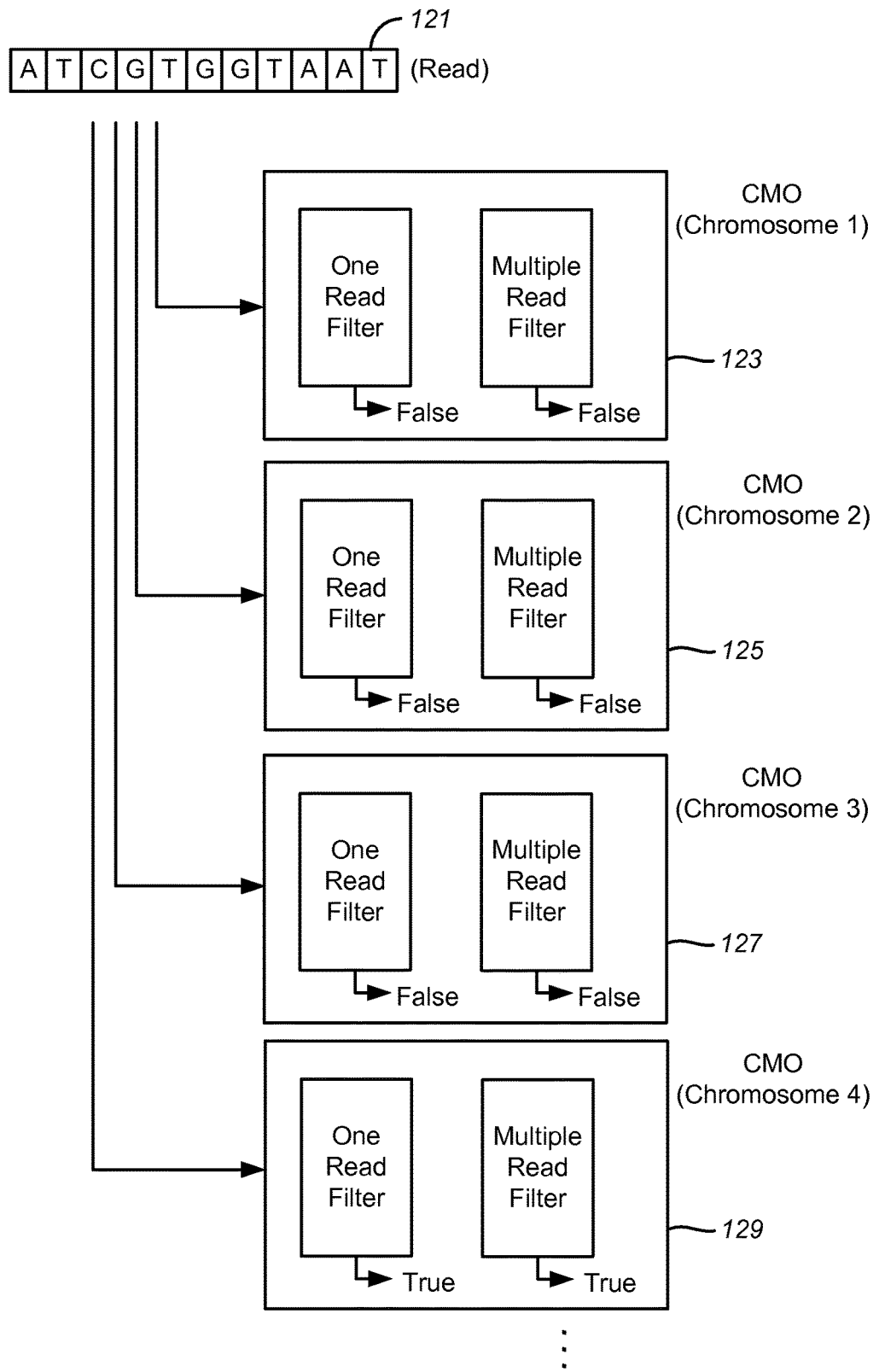

Finally, in the example depicted in FIG. 2D, it would appear that a valid alignment of read 121 occurs because only one of the One Read Filters, the one associated with Chromosome Membership Object 129, produces a true result. However, the Multiple Read Filter associated with object 129 also produces a true in response to its test. Therefore, the apparent alignment to chromosome 4 is deemed invalid.

While this description has focused on filters used to test membership in particular chromosomes, more granular testing may be employed in some embodiments. For example, a chromosome may be divided into sub-regions, such as strands, that provide useful information about the sample.

Figure 3A:
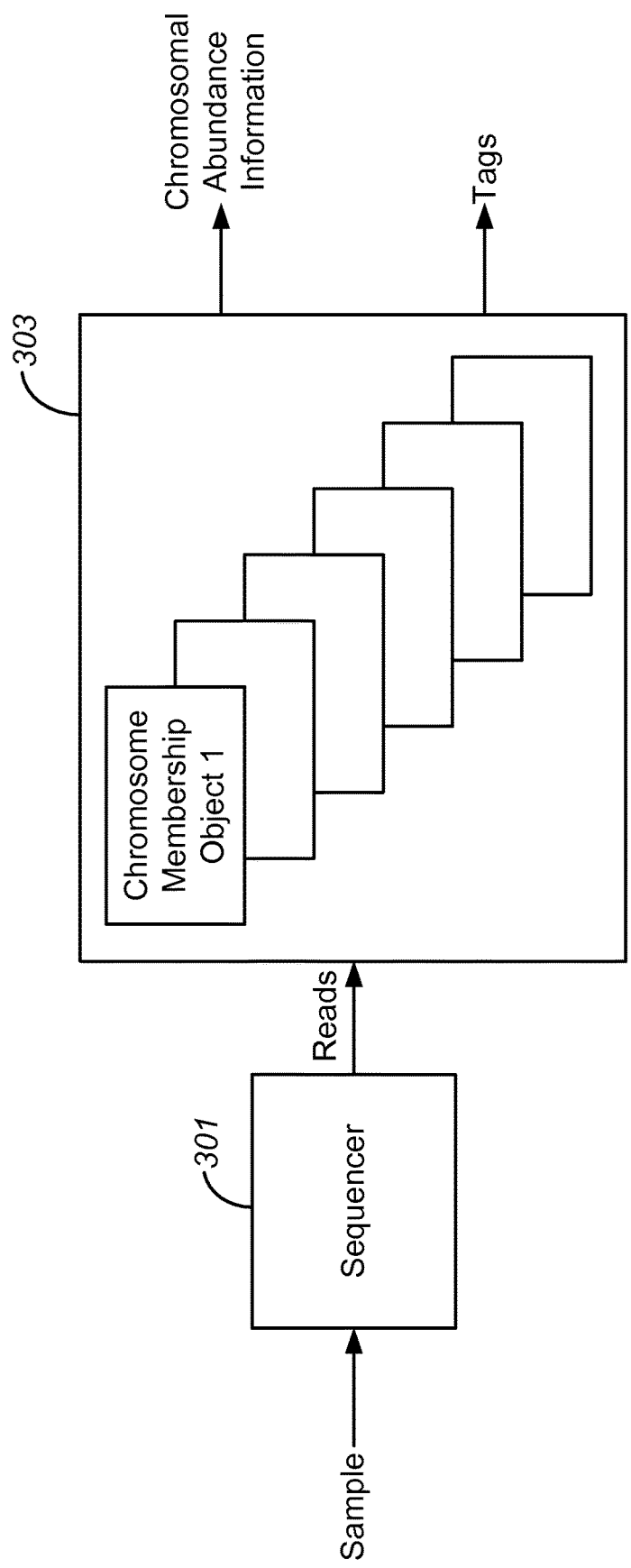
FIGS. 3A and 3B are block diagrams of the logical components of an alignment system (A) and a tool for creating an alignment filter (B).

FIG. 3A presents a block diagram showing certain logical components of an alignment system in accordance with certain embodiments. As shown, a sample is provided to a sequencer 301 which produces a series of reads from the sample. Various examples of sequencers are presented in the discussion below.

The reads are provided to a membership tester 303, which contains multiple Chromosome Membership Objects, each of which may have a structure as described in the context of FIGS. 2A through 2D. Each of these Chromosome Membership Objects will be associated with a different chromosome reference sequence of a genome reference sequence. Tester 303 includes the logic necessary for testing each of the reads from sequencer 301 against the Bloom filters in each of the Chromosome Membership Objects. Tester 303 outputs chromosomal abundance information and, optionally, various tags. Chromosomal abundance information indicates the number of reads that provide valid alignments with each of the chromosomes from the genomic reference sequence. The tags contain the sequence information from the reads and additional ancillary information such as the identity of the chromosomes to which the reads aligned validly.

Figure 3B:
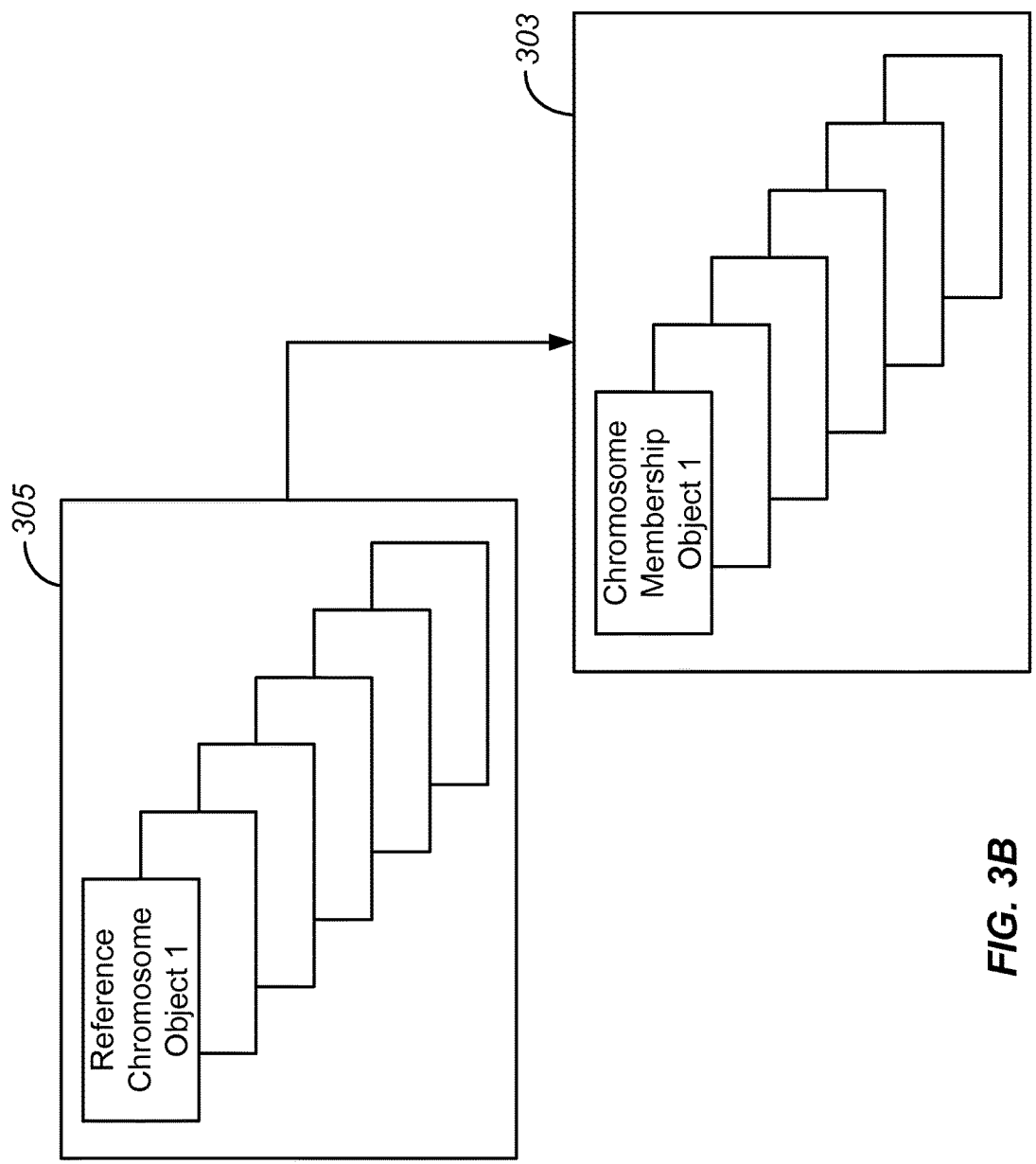

A system depicted in FIG. 3B includes a reference genome object 305. This object contains the logic necessary to generate the respective Bloom filters and Chromosome Membership Objects from the chromosome reference sequences that comprise the genomic reference sequence. In certain embodiments, this logic carves the chromosome reference sequences in to read sized slices which are fed to the Bloom filters' hash functions and used to populate the Bloom filters' bit arrays. FIG. 1A provides a simple example of how this can be accomplished.

In accordance with various implementations, alignment of a sample is accomplished in the following manner. Initially, a sample is treated to isolate its DNA. Thereafter, the nucleotide sequence from the isolated DNA is read. Typically, this involves reading fixed length sections of DNA. In some embodiments, this operation makes use of very fast sequencing tools such as massively parallel DNA sequencing tools as described below. In some cases, many thousands or millions of read sequences are read for a single sample. In specific examples, at least about one million read sequences are read and aligned, and in more specific examples, at least about five million sequences are read and mapped.

Figure 4:
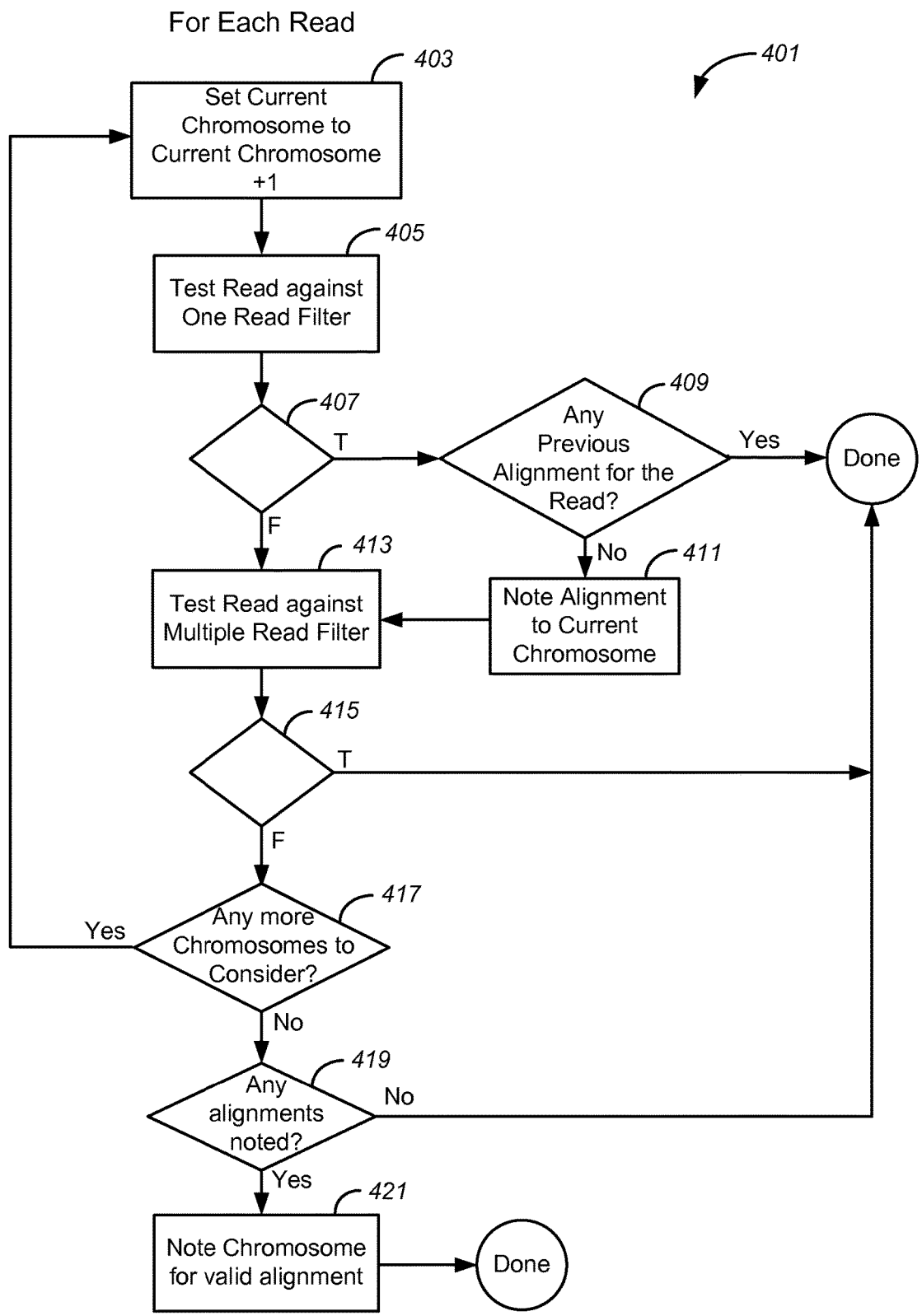
FIG. 4 is a flow chart for using chromosome alignment objects to align reads to a genomic reference sequence.

FIG. 4 presents a process flow chart 401 for implementing one embodiment of an aligner. The depicted aligner is used to align multiple reads from a sample nucleic acid to reference sequences of distinct chromosomes of an organism. The depicted flowchart illustrates the treatment of a single read taken from the sample. Initially, in an operation 403, a current chromosome is set for consideration. As illustrated by the loop to block 403, the current chromosome is incremented over the course of the process flow to all chromosomes to which the read might align. Any particular order of chromosomes may be appropriate. For example, all 23 of the human chromosomes may be separately considered in sequential order.

After the current chromosome has been set in operation 403, the process next tests the read under consideration against a One Read Filter for the chromosome under consideration. As explained, the One Read Filter is a Bloom filter for identifying reads having valid alignments to the reference sequence associated with the Bloom filter. A test of the filter will return a value of true or false depending upon whether the read under consideration matches any sequence that is a member of the filter. The test decision for the One Read Filter is depicted in an operation 407 in the flowchart.

If the test returns a value of true, which means that the read under consideration matches a sequence from the chromosome under consideration, the process next determines whether the read under consideration was previously found to align to any other chromosome. See decision block 409. It is entirely possible that, if the current chromosome is not the first chromosome to be considered in the process flow, that the read under consideration aligned to a different chromosome that was considered earlier. If this is the case, and decision block 409 is therefore answered in the affirmative, and it is assumed that the read under consideration should be discarded, in which case the process is terminated as illustrated. If, however, the read under consideration is found not to have aligned with any prior chromosome to this point in the process, the relevant logic will note the alignment to the current chromosome as illustrated at block 411.

If decision block 407 indicates that the read under consideration is not a member of the reference sequence associated with the one read filter, process control is directed to a block 413 which tests the read against a separate Bloom filter, a Multiple Read Filter, of the type described above. Similarly, if decision block 407 returns a value of true, and it was found that the current read was not previously aligned to any other chromosome, the read under consideration will be tested against the Multiple Read Filter at block 413. As explained, the Multiple Read Filter may allow testing for read sequences that should be automatically discarded because, for example, they belong to an excluded region or they were found to occur more than once in a given chromosome. Therefore, if the Multiple Read Filter test returns a value of true (see decision block 415), the process is terminated as indicated. However, if the Multiple Read Filter test returns a value of false, then the read under consideration is not discarded and the process continues as illustrated.

Assuming that the read under consideration has not been discarded (i.e., it does not align to the current Multiple Read Filter and it is not found to align to more than one chromosome after testing with the One Read Filter), the depicted process prepares to loop to the next chromosome under consideration. Thus, in the depicted embodiment, a decision block 417 determines whether there are any more chromosomes to consider for potential alignment. Assuming that there are other chromosomes to be considered, process control is directed back to block 403 where the current chromosome is incremented by one and the process continues as described above.

However, if all chromosomes have been considered and decision block 417 is answered in the negative, process control is directed to a decision block 419 which determines whether any alignments have been noted for the read under consideration. If each of the One Read Filters associated with each of the chromosomes returns a value of false, then block 419 is answered in the negative and the process is terminated without a valid alignment. By contrast, if decision block 419 is answered in the affirmative, then there is a single valid alignment for the read under consideration and the associated chromosome for that alignment is noted in a block 421. The process is then concluded with a valid alignment as illustrated.

Each of the multiple reads from a sample is treated in the same manner. This can give an indication of chromosomal abundance for the sample under consideration. Example code snippets for implementing a similar alignment method follow:

```
def align(read,genome):
    alignments = [ (chrom,chrom.align(read)) for chrom in genome ]
    hit = None
    for chrom,alignment in alignments:
        one_hit, mult_hit = alignment
        if mult_hit:
            return None
        elif one_hit:
            if hit is not None:
                return None
            else:
                hit = chrom
    return chrom
```

The following version is written in a format roughly following the Python programming language. The code employs a feature of Python referred to as "comprehensions" which is used to first create a map of all alignments, and then narrow the map down to just the hits.

```
def align(read,genome):
    alignments = { chrom: chrom.align(read) for chrom in genome }
    hits = [chrom for chrom,alignment in alignments.items( ) if True in alignment]
    if(True,True) in alignments.values( ):
        return None
    return hits[0] if len(hits) == 1 else None
```

As mentioned, at least two implementations employing Bloom filters to align reads may be employed. In a first one of these techniques, Bloom filters are created from the reference sequences prior to testing reads from any sample. One Bloom filter is produced for each location of interest (e.g., each chromosome) as explained above.

A read that aligns to one and only one location is deemed to have a valid alignment with that location. If a read aligns to zero or more than one location, it does not have a valid alignment and it is not considered for further treatment. Note that this particular aspect of alignment is limited to certain applications such as detection of aneuploidy. For some research applications, particularly those focused on genes rather than chromosomal abnormalities, it is desirable to consider information where a given read maps to multiple locations.

In a second implementation, the Bloom filter is used together with another alignment tool for aligning tags to locations in a reference sequence. The use of these two tools in conjunction with one another can be implemented in various ways. In one embodiment, a Bloom filter is used "in front of" an index tree. Specifically, a read under consideration is first applied to a Bloom filters for a particular chromosome or other location in the reference sequence. If a valid match is noted, the assignment is made and no use of the index tree is needed. However, if a read sequence does not map to the Bloom filter, it is applied to the index tree associated with the location under consideration to make a separate determine of whether it aligns. If it does and the assignment can be deemed to be valid, two things are done. First, the read is aligned with the location of the reference sequence. Second, the read hash values are added to the Bloom filter for the associated location in the reference sequence where the alignment occurred.

Example Applications

Various embodiments described herein, detect a trait under consideration (e.g., ploidy of particular human chromosomes) by aligning reads to reference sequences. These embodiments may be used to diagnose many types of conditions. In some cases, the alignment permits detection of aberrations in the trait under consideration (e.g., aneuploidy). In various embodiments, the source of sample DNA is blood or other bodily fluid from a pregnant individual. An aneuploidy of the fetus can be detected by comparing actual measured amounts of DNA aligning to a chromosome of interest to estimated amounts of such DNA for the sample. Detecting of more or less than the expected amount of DNA aligning to a particular chromosome can indicate fetal aneuploidy, e.g., detected variations in the amount of DNA mapping to any of human chromosomes 13, 16, 18 or 21. The method can similarly be used to determine a fetus' sex.

In some embodiments, the invention is used to determine the presence of absence of fetal anueploidy in a maternal plasma specimen containing a mixture of cell free maternal and fetal DNA. The presence of fetal aneuploidy by analysis of plasma cell free DNA can be determined, for example, according to the methods described in e.g. Fan et al., PNAS 105:16266-16271 [2008]; Chiu et al. PNAS 105:20458-20463 [2008]; Chiu et al., BMJ 2011; 342:c7401 [2011]; U.S. Patent Publication Nos. 2007/0202525 filed Feb. 2, 2007; 2009/0087847 filed Jul. 23, 2008; 2009/0029377 filed Jul. 23, 2008; 2008/0220422 filed Jun. 14, 2007; and 2008/0138809 filed Jun. 14, 2007, all of which are incorporated by reference in their entirety.

Figure 5:
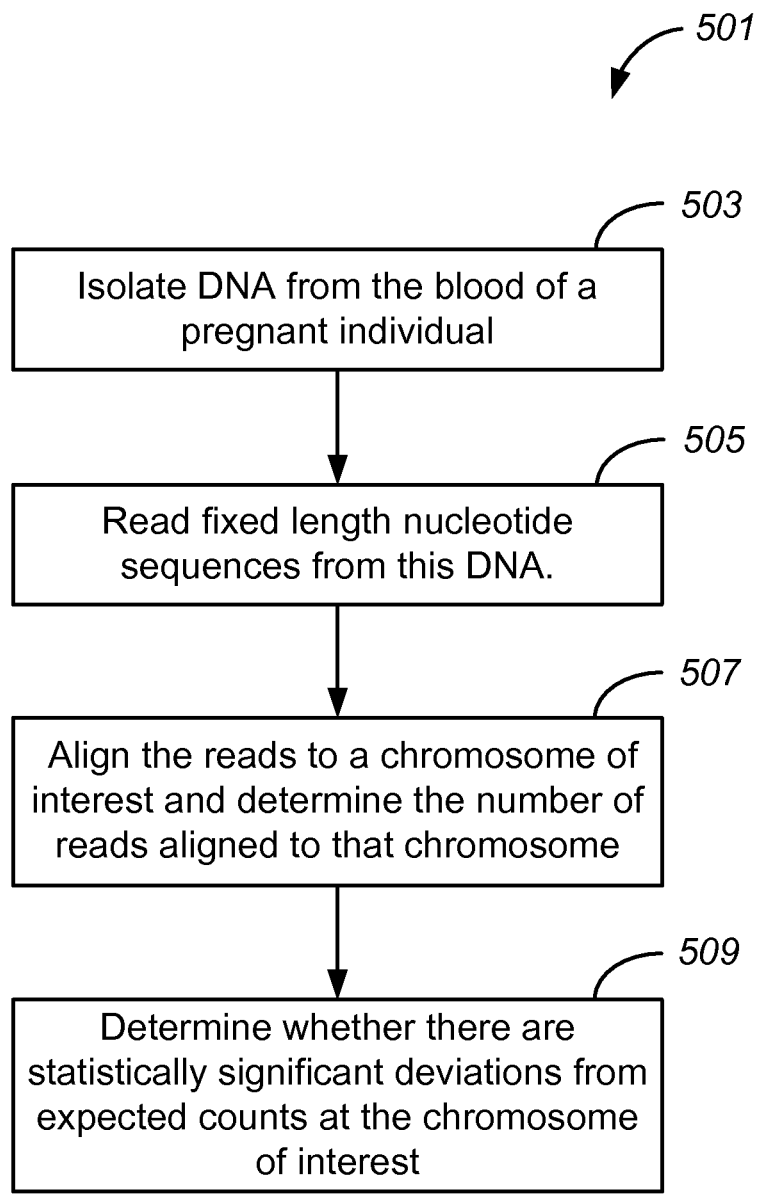
FIG. 5 is a flow chart representing a specific example for determining the sex or identifying aneuploidy in a fetus.

A specific example of a method for determining the sex or identifying aneuploidy in a fetus will now be described with reference to FIG. 5. As shown there, a test 501 begins with isolating DNA from the blood of a pregnant individual. See operation 503. This may be conducted using cell-bound or free DNA. It has been found that free DNA circulating in a mother's blood stream includes about 5 to 10% free DNA from the fetus carried by the mother. Many implementations of the method make use of cell-free DNA. Further, various implementations do not separate maternal DNA and fetal DNA or otherwise distinguish between the two.

After isolating the DNA in operation 503, the process involves reading nucleotide segments from this DNA. See operation 505. As explained, this involves reading fixed length sections of DNA, which are the reads. In some embodiments, this operation makes use of very fast sequencing tools such as massively parallel DNA sequencing tools. In some cases, many thousands or millions of sequences are read for a single sample. In specific examples, at least about one million sequences are read and aligned, and in more specific examples, at least about five million sequences are read and aligned.

Returning to FIG. 5, the reads are aligned to a chromosome of interest and the number of reads so aligned is determined. See operation 507. This may involve aligning each read to one of the 23 human chromosomes and determining the number of aligned reads per chromosome. For efficiency, the process need not store or analyze the sequence information from the reads. For example, the process need not identify SNPs in a DNA segment. Rather, operation 507 can simply provide a number of read sequences that align to a chromosome of interest.

In some embodiments, the method is performed without using a control sample. In other cases, the method provides an internal control which involves determining the number of reads aligning to a control chromosome. For example to detect aneuploidy, counts may be calculated for a both a chromosome suspected of aneuploidy and a chromosome that does not exhibit aneuploidy. A comparison of the calculated counts for these two chromosomes serves as an internal control. In a specific embodiment, one might compare the number of reads aligning to chromosomes 21 and 9, with the reads aligning to chromosome 9 serving as an internal control for aneuploidy detection in chromosome 21 (e.g., trisomy in chromosome 21).

It should be noted that the above-described technology may be based on a simple blood test and need not even distinguish maternal DNA from fetal DNA. It simply identifies statistically significant aberrations in the amount of DNA associated with different chromosomes in the free DNA circulating in maternal blood. The apparatus and associated software for performing the method quickly generates a read number associated with one or more of the 23 human chromosomes. This number need not, and preferably does not, distinguish maternal and fetal DNA. When the read numbers are complete and associated with the individual chromosomes, the relevant process algorithm identifies any statistically significant aberrations in the read counts. Other than the sex chromosomes, there should be two copies of each human chromosome. In other words, each of the non-sex chromosomes should be diploid. Any deviation from this is a manifestation of aneuploidy.

Of course, the methods and tools described herein are not limited to detection of aneuploidy. Generally, the methods and tools disclosed herein may be employed to detect a range of traits associated with an amount of a particular polynucleotide sequence within a plurality of sequences. The amount can be used to identify, in a quantitative or non-quantitative manner, a sequence such as a gene or a variant thereof. Variants include without limitation an allelic variation or a gene harboring a somatic mutation, such as a mutation linked to a cancer. The sequence can also identify a foreign sequence within the plurality of sequences, e.g., a microorganism such as a virus, bacteria or protozoan within a sample from a host. In some embodiments, the method is used to determine an amplification of a particular sequence, e.g., in the case of cancer. The copy number of a genetic structure, such as a chromosome or a gene, can be determined.

An amount of a genomic aberration in the subject can be assessed using the methods of the invention. The genomic aberration can be without limitation a fusion, deletion, insertion, mutation, aberrant methylation or other event. In some embodiments, the subject has been diagnosed with a proliferative disorder. For example, the proliferative disorder can be a cancer. It has been shown that blood plasma and serum DNA from cancer patients contains measurable quantities of tumor DNA, which can be recovered and used as surrogate source of tumor DNA. Tumors are characterized by aneuploidy, or inappropriate numbers of gene sequences or even entire chromosomes. The determination of a difference in the amount of a given sequence i.e. a sequence of interest, in a sample from an individual can thus be used in the diagnosis of a medical condition e.g. cancer.

Embodiments of the invention provide for a method to assess copy number variation of a sequence of interest e.g. a clinically-relevant sequence, in a test sample that comprises a mixture of nucleic acids derived from two different genomes, and which are known or are suspected to differ in the amount of one or more sequence of interest. The mixture of nucleic acids is derived from two or more types of cells. In one embodiment, the mixture of nucleic acids is derived from normal and cancerous cells derived from a subject suffering from a medical condition e.g. cancer.

It is believed that many solid tumors, such as breast cancer, progress from initiation to metastasis through the accumulation of several genetic aberrations. (Sato et al., Cancer Res., 50: 7184-7189 (1990); Jongsma et al., J Clin PAthol: Mol Path 55:305-309 (2002)), each incorporated herein by reference). Such genetic aberrations, as they accumulate, may confer proliferative advantages, genetic instability and the attendant ability to evolve drug resistance rapidly, and enhanced angiogenesis, proteolysis and metastasis. The genetic aberrations may affect either recessive "tumor suppressor genes" or dominantly acting oncogenes. Deletions and recombination leading to loss of heterozygosity (LOH) are believed to play a major role in tumor progression by uncovering mutated tumor suppressor alleles.

Cell free DNA ("cfDNA") has been found in the circulation of patients diagnosed with malignancies including but not limited to lung cancer (Pathak et al. Clin Chem 52:1833-1842 (2006)), prostate cancer (Schwartzenbach et al. Clin Cancer Res 15:1032-8 (2009)), and breast cancer (Schwartzenbach et al. available online at breast-cancer-research.com/content/11/5/R71 (2009)). Identification of genomic instabilities associated with cancers that can be determined in the circulating cfDNA in cancer patients is a potential diagnostic and prognostic tool. In one embodiment, the method of the invention assesses copy number variation ("CNV") of a sequence of interest in a sample comprising a mixture of nucleic acids derived from a subject that is suspected or is known to have cancer e.g. carcinoma, sarcoma, lymphoma, leukemia, germ cell tumors and blastoma. In one embodiment, the sample is a plasma sample derived from peripheral blood and that comprises a mixture of cfDNA derived from normal and cancerous cells. In another embodiment, the biological sample that is needed to determine whether a CNV is present is derived from a mixture of cancerous and non-cancerous cells from other biological fluids including but not limited to serum, sweat, tears, sputum, urine, sputum, ear flow, lymph, saliva, cerebrospinal fluid, ravages, bone marrow suspension, vaginal flow, transcervical lavage, brain fluid, ascites, milk, secretions of the respiratory, intestinal and genitourinary tracts, and leukophoresis samples, or in tissue biopsies, swabs or smears.

The sequence of interest is a nucleic acid sequence that is known or is suspected to play a role in the development and/or progression of the cancer. Examples of a sequence of interest include nucleic acids sequences that are amplified or deleted in cancerous cells as described in the following.

Dominantly acting genes associated with human solid tumors typically exert their effect by overexpression or altered expression. Gene amplification is a common mechanism leading to upregulation of gene expression. Evidence from cytogenetic studies indicates that significant amplification occurs in over 50% of human breast cancers. Most notably, the amplification of the proto-oncogene human epidermal growth factor receptor 2 (HER2) located on chromosome 17 (17(17q21-q22)), results in overexpression of HER2 receptors on the cell surface leading to excessive and dysregulated signaling in breast cancer and other malignancies (Park et al., Clinical Breast Cancer 8:392-401 (2008) incorporated herein by reference). A variety of oncogenes have been found to be amplified in other human malignancies. Examples of the amplification of cellular oncogenes in human tumors include amplifications of: c-myc in promyelocytic leukemia cell line HL60, and in small-cell lung carcinoma cell lines, N-myc in primary neuroblastomas (stages III and IV), neuroblastoma cell lines, retinoblastoma cell line and primary tumors, and small-cell lung carcinoma lines and tumors, L-myc in small-cell lung carcinoma cell lines and tumors, c-myb in acute myeloid leukemia and in colon carcinoma cell lines, c-erbb in epidermoid carcinoma cell, and primary gliomas, c-K-ras-2 in primary carcinomas of lung, colon, bladder, and rectum, N-ras in mammary carcinoma cell line (Varmus H., Ann Rev Genetics 18: 553-612 (1984) (cited in Watson et al., Molecular Biology of the Gene (4th ed.; Benjamin/Cummings Publishing Co. 1987), each incorporated herein by reference).

Chromosomal deletions involving tumor suppressor genes may play an important role in the development and progression of solid tumors. The retinoblastoma tumor suppressor gene (Rb-1), located in chromosome 13q14, is the most extensively characterized tumor suppressor gene. The Rb-1 gene product, a 105 kDa nuclear phosphoprotein, apparently plays an important role in cell cycle regulation (Howe et al., Proc Natl Acad Sci (USA) 87:5883-5887 (1990), incorporated herein by reference). Altered or lost expression of the Rb protein is caused by inactivation of both gene alleles either through a point mutation or a chromosomal deletion. Rb-i gene alterations have been found to be present not only in retinoblastomas but also in other malignancies such as osteosarcomas, small cell lung cancer (Rygaard et al., Cancer Res 50: 5312-5317 (1990)), incorporated herein by reference) and breast cancer. Restriction fragment length polymorphism (RFLP) studies have indicated that such tumor types have frequently lost heterozygosity at 13q suggesting that one of the Rb-1 gene alleles has been lost due to a gross chromosomal deletion (Bowcock et al., Am J Hum Genet, 46: 12 (1990), incorporated herein by reference). Chromosome 1 abnormalities including duplications, deletions and unbalanced translocations involving chromosome 6 and other partner chromosomes indicate that regions of chromosome 1, in particular 1q21-1q32 and 1p11-13, might harbor oncogenes or tumor suppressor genes that are pathogenetically relevant to both chronic and advanced phases of myeloproliferative neoplasms (Caramazza et al., Eur J Hematol 84:191-200 (2010), incorporated herein by reference). Myeloproliferative neoplasms are also associated with deletions of chromosome 5. Complete loss or interstitial deletions of chromosome 5 are the most common karyotypic abnormality in myelodysplastic syndromes (MDSs). Isolated del(5q)/5q-MDS patients have a more favorable prognosis than those with additional karyotypic defects, who tend to develop myeloproliferative neoplasms (MPNs) and acute myeloid leukemia. The frequency of unbalanced chromosome 5 deletions has led to the idea that 5q harbors one or more tumor-suppressor genes that have fundamental roles in the growth control of hematopoietic stem/progenitor cells (HSCs/HPCs). Cytogenetic mapping of commonly deleted regions (CDRs) centered on 5q31 and 5q32 identified candidate tumor-suppressor genes, including the ribosomal subunit RPS14, the transcription factor Egr1/Krox20 and the cytoskeletal remodeling protein, alpha-catenin (Eisenmann et al., Oncogene 28:3429-3441 (2009), each incorporated herein by reference). Cytogenetic and allelotyping studies of fresh tumors and tumor cell lines have shown that allelic loss from several distinct regions on chromosome 3p, including 3p25, 3p21-22, 3p21.3, 3p12-13 and 3p14, are the earliest and most frequent genomic abnormalities involved in a wide spectrum of major epithelial cancers of lung, breast, kidney, head and neck, ovary, cervix, colon, pancreas, esophagus, bladder and other organs. Several tumor suppressor genes have been mapped to the chromosome 3p region, and are thought that interstitial deletions or promoter hypermethylation precede the loss of the 3p or the entire chromosome 3 in the development of carcinomas (Angeloni D., Briefings Functional Genomics 6:19-39 (2007), incorporated herein by reference).

Newborns and children with Down syndrome (DS) often present with congenital transient leukemia and have an increased risk of acute myeloid leukemia and acute lymphoblastic leukemia. Chromosome 21, harboring about 300 genes, may be involved in numerous structural aberrations, e.g., translocations, deletions, and amplifications, in leukemias, lymphomas, and solid tumors. Moreover, genes located on chromosome 21 have been identified that play an important role in tumorigenesis. Somatic numerical as well as structural chromosome 21 aberrations are associated with leukemias, and specific genes including RUNX1, TMPRSS2, and TFF, which are located in 21q, play a role in tumorigenesis (Fonatsch C Gene Chromosomes Cancer 49:497-508 (2010), incorporated herein by reference).

In one embodiment, some of the methods described herein provide a means to assess the association between gene amplification and the extent of tumor evolution. Correlation between amplification and/or deletion and stage or grade of a cancer may be prognostically important because such information may contribute to the definition of a genetically based tumor grade that would better predict the future course of disease with more advanced tumors having the worst prognosis. In addition, information about early amplification and/or deletion events may be useful in associating those events as predictors of subsequent disease progression. Gene amplification and deletions as identified by methods disclosed herein can be associated with other known parameters such as tumor grade, histology, Brd/Urd labeling index, hormonal status, nodal involvement, tumor size, survival duration and other tumor properties available from epidemiological and bio statistical studies. For example, tumor DNA to be tested by these methods could include atypical hyperplasia, ductal carcinoma in situ, stage I-III cancer and metastatic lymph nodes in order to permit the identification of associations between amplifications and deletions and stage. The associations made may make possible effective therapeutic intervention. For example, consistently amplified regions may contain an overexpressed gene, the product of which may be able to be attacked therapeutically (for example, the growth factor receptor tyrosine kinase, p185$^{HER2}$).

The methods can be used to identify amplification and/or deletion events that are associated with drug resistance by determining the copy number variation of nucleic acids from primary cancers to those of cells that have metastasized to other sites. If gene amplification and/or deletion is a manifestation of karyotypic instability that allows rapid development of drug resistance, more amplification and/or deletion in primary tumors from chemo resistant patients than in tumors in chemo sensitive patients would be expected. For example, if amplification of specific genes is responsible for the development of drug resistance, regions surrounding those genes would be expected to be amplified consistently in tumor cells from pleural effusions of chemo resistant patients but not in the primary tumors. Discovery of associations between gene amplification and/or deletion and the development of drug resistance may allow the identification of patients that will or will not benefit from adjuvant therapy. (See pending U.S. patent application Ser. No. 12/958,352 filed Dec. 1, 2010, and Ser. No. 12/958,353 filed Dec. 1, 2010, incorporated herein by reference).

Thus, in general, the aberration under consideration can be causative or only indicative of the proliferative disorder. In some embodiments, the sample comprises or is suspected to comprise tumor cells. In some embodiments, the sample is bodily fluid, e.g., blood. In an exemplary embodiment, the methods of the invention are used to determine an amount of tumor DNA circulating in the blood of a subject diagnosed with a proliferative disorder. In some embodiments, the suspect is suspected but not confirmed to have the disorder. The methods can be used in the diagnosis of the disorder.

In some embodiments, the variance of the detection of specific sequences corresponding to a chromosome is less than about 20%, 15%, 10%, 9%, 8%, 7%, 6%, 5%, 4%, 3%, 2%, 1%, 0.9%, 0.8%, 0.7%, 0.6%, 0.5%, 0.4%, 0.3%, 0.2%, or less than about 0.1%.

In certain aspects concerning methods for determining fetal aneuploidy from a maternal sample, the methods include comparing the distribution of a plurality of polynucleotide sequences reads from a sample with an expected distribution based on estimated fetal DNA concentration in the maternal sample. In embodiments, the method has a precision of at least 60%, 65%, 70%, 75%, 80%, 85%, 90%, 91%, 92%, 93%, 94%, 95%, 96%, 97%, 98%, or at least 99%. In embodiments, the method uses the methodology provided herein to determine a normalized amount of a fetal polynucleotide found within a maternal blood sample. The amounts of the fetal chromosomes can be compared to the expected amounts to determine fetal aneuploidy. The expected amounts may include without limitation the amounts of fetal DNA expected if the fetus is male or female, or if the fetus has or does not have an aneuploidy or other chromosomal abnormality.

Sample Sequencing

In some embodiments, the methods employ PCR or a related technique for amplifying sample nucleotide sequences before identifying or aligning them. In various embodiments, the method described herein employs next generation sequencing technology (NGS) in which clonally amplified DNA templates or single DNA molecules are sequenced in a massively parallel fashion within a flow cell (e.g. as described in Volkerding et al. Clin Chem 55:641-658 [2009]; Metzker M Nature Rev 11:31-46 [2010]). In addition to high-throughput sequence information, NGS provides digital quantitative information, in that each sequence read is a countable "sequence tag" representing an individual clonal DNA template or a single DNA molecule. The sequencing technologies of NGS include gyro sequencing, sequencing-by-synthesis with reversible dye terminators, sequencing by oligonucleotide probe ligation and real time sequencing.

Some of the sequencing technologies are available commercially, such as the sequencing-by-hybridization platform from Affymetrix Inc. (Sunnyvale, Calif.) and the sequencing-by-synthesis platforms from 454 Life Sciences (Bradford, Conn.), Illumina/Solexa (Hayward, Calif.) and Helicos Biosciences (Cambridge, Mass.), and the sequencing-by-ligation platform from Applied Biosystems (Foster City, Calif.), as described below. In addition to the single molecule sequencing performed using sequencing-by-synthesis of Helicos Biosciences, other single molecule sequencing technologies are encompassed by the disclosed method and include the SMRT™ technology of Pacific Biosciences, the Ion Torrent™ technology, and nanopore sequencing being developed for example, by Oxford Nanopore Technologies.

While the automated Sanger method is considered as a 'first generation' technology, Sanger sequencing including the automated Sanger sequencing, can also be employed by the disclosed method. Additional sequencing methods that comprise the use of developing nucleic acid imaging technologies e.g. atomic force microscopy (AFM) or transmission electron microscopy (TEM), are also encompassed by the disclosed method. Exemplary sequencing technologies are described below.

In one embodiment, the DNA sequencing technology that is used in the disclosed methods is the Helicos True Single Molecule Sequencing (tSMS) (e.g. as described in Harris T. D. et al., Science 320:106-109 [2008]). In the tSMS technique, a DNA sample is cleaved into strands of approximately 100 to 200 nucleotides, and a polyA sequence is added to the 3' end of each DNA strand. Each strand is labeled by the addition of a fluorescently labeled adenosine nucleotide. The DNA strands are then hybridized to a flow cell, which contains millions of oligo-T capture sites that are immobilized to the flow cell surface. The templates can be at a density of about 100 million templates/cm$^2$. The flow cell is then loaded into an instrument, e.g., HeliScope™ sequencer, and a laser illuminates the surface of the flow cell, revealing the position of each template. A CCD camera can map the position of the templates on the flow cell surface. The template fluorescent label is then cleaved and washed away. The sequencing reaction begins by introducing a DNA polymerase and a fluorescently labeled nucleotide. The oligo-T nucleic acid serves as a primer. The polymerase incorporates the labeled nucleotides to the primer in a template directed manner. The polymerase and unincorporated nucleotides are removed. The templates that have directed incorporation of the fluorescently labeled nucleotide are discerned by imaging the flow cell surface. After imaging, a cleavage step removes the fluorescent label, and the process is repeated with other fluorescently labeled nucleotides until the desired read length is achieved. Sequence information is collected with each nucleotide addition step. Whole genome sequencing by single molecule sequencing technologies excludes PCR-based amplification in the preparation of the sequencing libraries, and the directness of sample preparation allows for direct measurement of the sample, rather than measurement of copies of that sample.

In one embodiment, the DNA sequencing technology that is used in the disclosed methods is the 454 sequencing (Roche) (e.g. as described in Margulies, M. et al. Nature 437:376-380 (2005)). 454 sequencing involves two steps. In the first step, DNA is sheared into fragments of approximately 300-800 base pairs, and the fragments are blunt-ended. Oligonucleotide adaptors are then ligated to the ends of the fragments. The adaptors serve as primers for amplification and sequencing of the fragments. The fragments can be attached to DNA capture beads, e.g., streptavidin-coated beads using, e.g., Adaptor B, which contains 5'-biotin tag. The fragments attached to the beads are PCR amplified within droplets of an oil-water emulsion. The result is multiple copies of clonally amplified DNA fragments on each bead. In the second step, the beads are captured in wells (pico-liter sized). Pyro sequencing is performed on each DNA fragment in parallel. Addition of one or more nucleotides generates a light signal that is recorded by a CCD camera in a sequencing instrument. The signal strength is proportional to the number of nucleotides incorporated. Pyro sequencing makes use of pyrophosphate (PPi) which is released upon nucleotide addition. PPi is converted to ATP by ATP sulfurylase in the presence of adenosine 5' phosphosulfate. Luciferase uses ATP to convert luciferin to oxyluciferin, and this reaction generates light that is discerned and analyzed.

In one embodiment, the DNA sequencing technology that is used in the disclosed methods is the SOLiD™ technology (Applied Biosystems). In SOLiD™ sequencing-by-ligation, genomic DNA is sheared into fragments, and adaptors are attached to the 5' and 3' ends of the fragments to generate a fragment library. Alternatively, internal adaptors can be introduced by ligating adaptors to the 5' and 3' ends of the fragments, circularizing the fragments, digesting the circularized fragment to generate an internal adaptor, and attaching adaptors to the 5' and 3' ends of the resulting fragments to generate a mate-paired library. Next, clonal bead populations are prepared in micro reactors containing beads, primers, template, and PCR components. Following PCR, the templates are denatured and beads are enriched to separate the beads with extended templates. Templates on the selected beads are subjected to a 3' modification that permits bonding to a glass slide. The sequence can be determined by sequential hybridization and ligation of partially random oligonucleotides with a central determined base (or pair of bases) that is identified by a specific fluorophore. After a color is recorded, the ligated oligonucleotide is cleaved and removed and the process is then repeated.

In one embodiment, the DNA sequencing technology that is used in the disclosed methods is the single molecule, real-time (SMRT™) sequencing technology of Pacific Biosciences. In SMRT sequencing, the continuous incorporation of dye-labeled nucleotides is imaged during DNA synthesis. Single DNA polymerase molecules are attached to the bottom surface of individual zero-mode wavelength identifiers (ZMW identifiers) that obtain sequence information while phospholinked nucleotides are being incorporated into the growing primer strand. A ZMW is a confinement structure which enables observation of incorporation of a single nucleotide by DNA polymerase against the background of fluorescent nucleotides that rapidly diffuse in an out of the ZMW (in microseconds). It takes several milliseconds to incorporate a nucleotide into a growing strand. During this time, the fluorescent label is excited and produces a fluorescent signal, and the fluorescent tag is cleaved off. Identification of the corresponding fluorescence of the dye indicates which base was incorporated. The process is repeated.

In one embodiment, the DNA sequencing technology that is used in the disclosed methods is nanopore sequencing (e.g. as described in Soni G V and Meller A. Clin Chem 53: 1996-2001 [2007]). Nanopore sequencing DNA analysis techniques are being industrially developed by a number of companies, including Oxford Nanopore Technologies (Oxford, United Kingdom). Nanopore sequencing is a single-molecule sequencing technology whereby a single molecule of DNA is sequenced directly as it passes through a nanopore. A nanopore is a small hole, of the order of 1 nanometer in diameter. Immersion of a nanopore in a conducting fluid and application of a potential (voltage) across it results in a slight electrical current due to conduction of ions through the nanopore. The amount of current which flows is sensitive to the size and shape of the nanopore. As a DNA molecule passes through a nanopore, each nucleotide on the DNA molecule obstructs the nanopore to a different degree, changing the magnitude of the current through the nanopore in different degrees. Thus, this change in the current as the DNA molecule passes through the nanopore represents a reading of the DNA sequence.

In one embodiment, the DNA sequencing technology that is used in the disclosed methods is the chemical-sensitive field effect transistor (chemFET) array (e.g., as described in U.S. Patent Publication No. 2009/0026082 filed Dec. 17, 2007). In one example of the technique, DNA molecules can be placed into reaction chambers, and the template molecules can be hybridized to a sequencing primer bound to a polymerase. Incorporation of one or more triphosphates into a new nucleic acid strand at the 3' end of the sequencing primer can be discerned by a change in current by a chemFET. An array can have multiple chemFET sensors. In another example, single nucleic acids can be attached to beads, and the nucleic acids can be amplified on the bead, and the individual beads can be transferred to individual reaction chambers on a chemFET array, with each chamber having a chemFET sensor, and the nucleic acids can be sequenced.

In one embodiment, the DNA sequencing technology that is used in the disclosed methods is the Halcyon Molecular's method that uses transmission electron microscopy (TEM). The method, termed Individual Molecule Placement Rapid Nano Transfer (IMPRNT), comprises utilizing single atom resolution transmission electron microscope imaging of high-molecular weight (150 kb or greater) DNA selectively labeled with heavy atom markers and arranging these molecules on ultra-thin films in ultra-dense (3 nm strand-to-strand) parallel arrays with consistent base-to-base spacing. The electron microscope is used to image the molecules on the films to determine the position of the heavy atom markers and to extract base sequence information from the DNA. The method is further described in PCT patent publication WO 2009/046445. The method allows for sequencing complete human genomes in less than ten minutes.

In one embodiment, the DNA sequencing technology is the Ion Torrent single molecule sequencing, which pairs semiconductor technology with a simple sequencing chemistry to directly translate chemically encoded information (A, C, G, T) into digital information (0, 1) on a semiconductor chip. In nature, when a nucleotide is incorporated into a strand of DNA by a polymerase, a hydrogen ion is released as a byproduct. Ion Torrent uses a high-density array of micro-machined wells to perform this biochemical process in a massively parallel way. Each well holds a different DNA molecule. Beneath the wells is an ion-sensitive layer and beneath that an ion sensor. When a nucleotide, for example a C, is added to a DNA template and is then incorporated into a strand of DNA, a hydrogen ion will be released. The charge from that ion will change the pH of the solution, which can be identified by Ion Torrent's ion sensor. The sequencer—essentially the world's smallest solid-state pH meter—calls the base, going directly from chemical information to digital information. The Ion personal Genome Machine (PGM™) sequencer then sequentially floods the chip with one nucleotide after another. If the next nucleotide that floods the chip is not a match. No voltage change will be recorded and no base will be called. If there are two identical bases on the DNA strand, the voltage will be double, and the chip will record two identical bases called. Direct identification allows recordation of nucleotide incorporation in seconds.

Other sequencing methods include digital PCR and sequencing by hybridization. Digital polymerase chain reaction (digital PCR or dPCR) can be used to directly identify and quantify nucleic acids in a sample. Digital PCR can be performed in an emulsion. Individual nucleic acids are separated, e.g., in a microfluidic chamber device, and each nucleic acid is individually amplified by PCR. Nucleic acids can be separated such there is an average of approximately 0.5 nucleic acids/well, or not more than one nucleic acid/well. Different probes can be used to distinguish fetal alleles and maternal alleles. Alleles can be enumerated to determine copy number. In sequencing by hybridization, the hybridization comprises contacting the plurality of polynucleotide sequences with a plurality of polynucleotide probes, wherein each of the plurality of polynucleotide probes can be optionally tethered to a substrate. The substrate might be flat surface comprising an array of known nucleotide sequences. The pattern of hybridization to the array can be used to determine the polynucleotide sequences present in the sample. In other embodiments, each probe is tethered to a bead, e.g., a magnetic bead or the like. Hybridization to the beads can be identified and used to identify the plurality of polynucleotide sequences within the sample.

In one embodiment, the method employs massively parallel sequencing of millions of DNA fragments using Illumina's sequencing-by-synthesis and reversible terminator-based sequencing chemistry (e.g. as described in Bentley et al., Nature 6:53-59 [2009]). Template DNA can be genomic DNA e.g. cfDNA. In some embodiments, genomic DNA from isolated cells is used as the template, and it is fragmented into lengths of several hundred base pairs. In other embodiments, cfDNA is used as the template, and fragmentation is not required as cfDNA exists as short fragments. For example fetal cfDNA circulates in the bloodstream as fragments of <300 bp, and maternal cfDNA has been estimated to circulate as fragments of between about 0.5 and 1 Kb (Li et al., Clin Chem, 50: 1002-1011 (2004)). Illumina's sequencing technology relies on the attachment of fragmented genomic DNA to a planar, optically transparent surface on which oligonucleotide anchors are bound. Template DNA is end-repaired to generate 5'-phosphorylated blunt ends, and the polymerase activity of Klenow fragment is used to add a single A base to the 3' end of the blunt phosphorylated DNA fragments. This addition prepares the DNA fragments for ligation to oligonucleotide adapters, which have an overhang of a single T base at their 3' end to increase ligation efficiency. The adapter oligonucleotides are complementary to the flow-cell anchors. Under limiting-dilution conditions, adapter-modified, single-stranded template DNA is added to the flow cell and immobilized by hybridization to the anchors. Attached DNA fragments are extended and bridge amplified to create an ultra-high density sequencing flow cell with hundreds of millions of clusters, each containing ~1,000 copies of the same template. In one embodiment, the randomly fragmented genomic DNA e.g. cfDNA, is amplified using PCR before it is subjected to cluster amplification. Alternatively, an amplification-free genomic library preparation is used, and the randomly fragmented genomic DNA e.g. cfDNA is enriched using the cluster amplification alone (Kozarewa et al., Nature Methods 6:291-295 [2009]). The templates are sequenced using a robust four-color DNA sequencing-by-synthesis technology that employs reversible terminators with removable fluorescent dyes. High-sensitivity fluorescence identification is achieved using laser excitation and total internal reflection optics. Short sequence reads of about 20-40 bp e.g. 36 bp, are aligned against a repeat-masked reference genome and genetic differences are called using specially developed data analysis pipeline software. After completion of the first read, the templates can be regenerated in situ to enable a second read from the opposite end of the fragments. Thus, either single-end or paired end sequencing of the DNA fragments is used according to the method. Partial sequencing of DNA fragments present in the sample is performed, and sequence tags comprising reads of predetermined length e.g. 36 bp, that are aligned to a known reference genome are counted.

The length of the sequence read is associated with the particular sequencing technology. NGS methods provide sequence reads that vary in size from tens to hundreds of base pairs. In some embodiments of the method described herein, the sequence reads are about 20 bp, about 25 bp, about 30 bp, about 35 bp, about 40 bp, about 45 bp, about 50 bp, about 55 bp, about 60 bp, about 65 bp, about 70 bp, about 75 bp, about 80 bp, about 85 bp, about 90 bp, about 95 bp, about 100 bp, about 110 bp, about 120 bp, about 130, about 140 bp, about 150 bp, about 200 bp, about 250 bp, about 300 bp, about 350 bp, about 400 bp, about 450 bp, or about 500 bp. It is expected that technological advances will enable single-end reads of greater than 500 bp enabling for reads of greater than about 1000 bp when paired end reads are generated. In one embodiment, the sequence reads are 36 bp. Other sequencing methods that can be employed by the disclosed methods include the single molecule sequencing methods that can sequence nucleic acids molecules >5000 bp. The massive quantity of sequence output is transferred by an analysis pipeline that transforms primary imaging output from the sequencer into strings of bases. A package of integrated algorithms performs the core primary data transformation steps: image analysis, intensity scoring, base calling, and alignment.

Apparatus

As should be apparent, certain embodiments employ processes involving data stored in or transferred through one or more computer systems or other processing systems. Embodiments of the invention also relate to apparatus for performing these operations. This apparatus may be specially constructed for the required purposes, or it may be a general-purpose computer (or a collection on networked computers) selectively activated or reconfigured by a computer program and/or data structure stored in the computer.

In addition, embodiments of the present invention relate to tangible and/or non-transitory computer readable media or computer program products that include program instructions and/or data (including data structures) for performing various computer-implemented operations. Examples of computer-readable media include, but are not limited to, magnetic media such as disk drives, semiconductor memory devices, magnetic tape, optical media such as CDs, magneto-optical media, and hardware devices that are specially configured to store and perform program instructions, such as read-only memory devices (ROM) and random access memory (RAM). Examples of program instructions include both machine code, such as produced by a compiler, and files containing higher level code that may be executed by the computer using an interpreter.

In certain embodiments, the disclosed methods make use of a stored Bloom filter or other set membership tester concerning reference sequences to be analyzed. As explained above, the sequences from the sample under consideration can be aligned or otherwise mapped to the reference sequences. In various embodiments, the reference sequences are stored in a database such as a relational or object database, for example.

Figure 6:
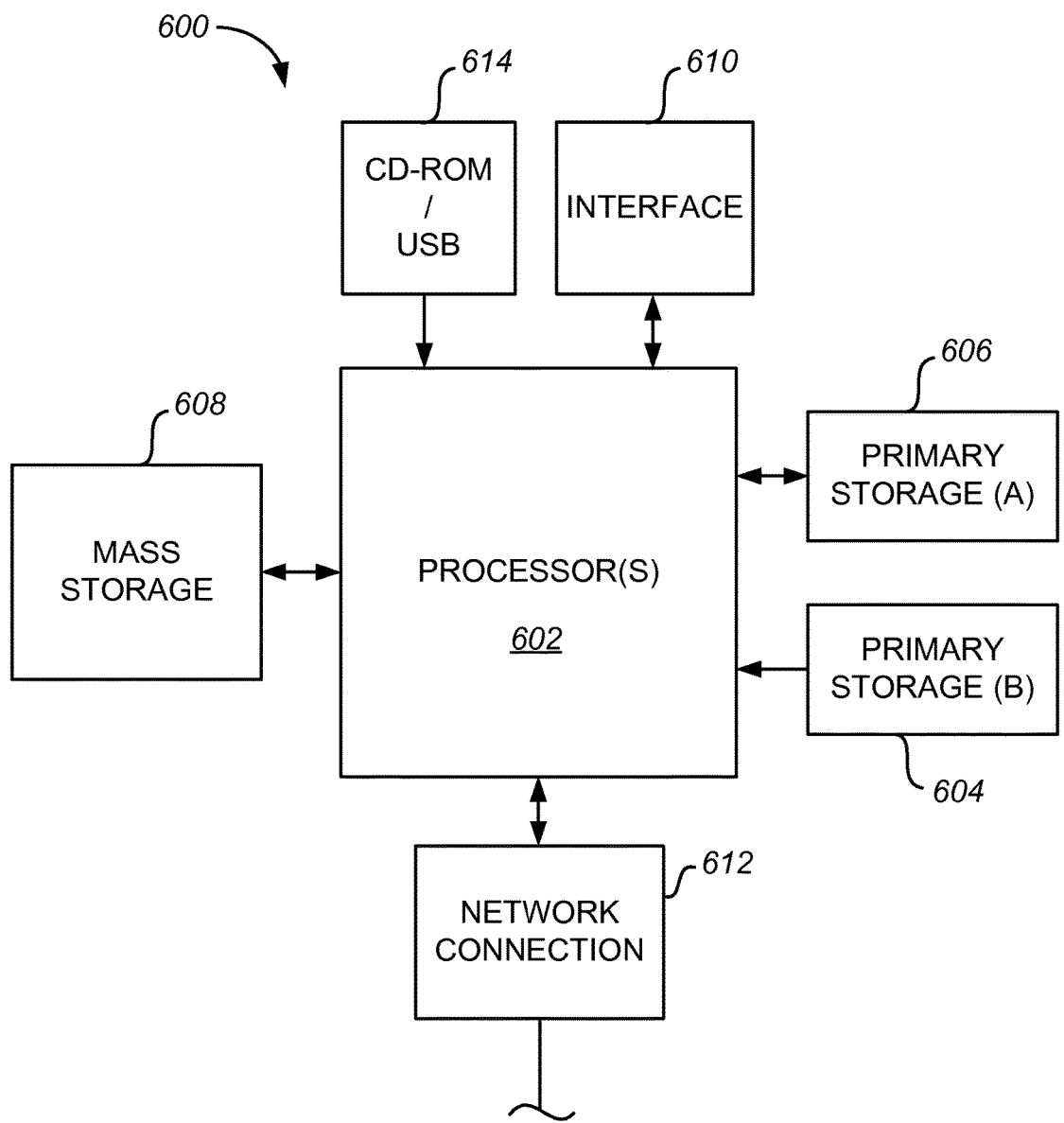
FIG. 6 is block diagram of a computer system suitable for use with the present invention.

FIG. 6 illustrates a typical computer system that, when appropriately configured or designed, can serve as an analysis apparatus of this invention. The computer system 600 includes any number of processors 602 (also referred to as central processing units, or CPUs) that are coupled to storage devices including primary storage 606 (typically a random access memory, or RAM) and primary storage 604 (e.g., read only memory or ROM). CPU 602 may be of various types including microcontrollers and microprocessors such as programmable devices (e.g., CPLDs and FPGAs) and unprogrammable devices such as gate array ASICs or general purpose microprocessors. As is well known in the art, primary storage 604 acts to transfer data and instructions to the CPU and primary storage 606 is used typically to transfer data and instructions in a bi-directional manner. Both of these primary storage devices may include any suitable computer-readable media such as those described above. A mass storage device 608 is also coupled bi-directionally to CPU 602 and provides additional data storage capacity and may include any of the computer-readable media described above. Mass storage device 608 may be used to store programs, data and the like and is typically a secondary storage medium such as a magnetic hard disk or high density semiconductor memory. It will be appreciated that the information retained within the mass storage device 608 may, in appropriate cases, be incorporated in standard fashion as part of primary storage 606 as virtual memory. A specific mass storage device such as a removable semiconductor memory or CD-ROM 614 may also pass data uni-directionally to the CPU.

CPU 602 is also coupled to an interface 610 that connects to one or more input/output devices such as such as video monitors, mice, keyboards, microphones, touch-sensitive displays, transducer card readers, tablets, styluses, voice or handwriting recognizers, or other well-known input devices such as, of course, other computers. Finally, CPU 602 optionally may be coupled to an external device such as a database or a computer or telecommunications network using an external connection as shown generally at 612. With such a connection, it is contemplated that the CPU might receive information from the network, or might output information to the network in the course of performing the method steps described herein.

Sequence or other data, can be input into a computer by a user either directly or indirectly. In one embodiment, the computer system 600 is directly coupled to a sequencing tool that reads and/or analyzes sequences of amplified nucleic acids. Sequences or other information from such tools are provided via interface 612 for analysis by system 600. Alternatively, the sequences processed by system 600 are provided from a sequence storage source such as a database or other repository. Once in the processing apparatus 600, a memory device such as primary storage 606 or mass storage 608 buffers or stores, at least temporarily, sequences of the nucleic acids. In addition, the memory device may store reads counts for various chromosomes or genomes, Bloom filters, etc. The memory may also store various routines and/or programs for analyzing the presenting the sequence or mapped data. Such programs/routines may include programs for performing statistical analyses, etc.

In one example, a user provides a sample into a sequencing apparatus. Data is collected and/or analyzed by the sequencing apparatus which is connected to a computer. Software on the computer allows for data collection and/or analysis. Data can be stored, displayed (via a monitor or other similar device), and/or sent to another location. As indicated, the computer may be connected to the internet which is used to transmit data to a handheld device utilized by a remote user (e.g., a physician, scientist or analyst). It is understood that the data can be stored and/or analyzed prior to transmittal. In some embodiments, raw data is collected and sent to a remote user (or apparatus) who will analyze and/or store the data. Transmittal can occur via the internet, but can also occur via satellite or other connection. Alternately, data can be stored on a computer-readable medium (e.g., CD or semiconductor memory storage device) and the medium can be shipped to an end user (e.g., via mail). The remote user can be in the same or a different geographical location including, but not limited to a building, city, state, country or continent.

In some embodiments, the methods also include collecting data regarding a plurality of polynucleotide sequences (e.g., reads and/or reference sequences) and sending the data to a computer such as system 600. For example, the computer can be connected to laboratory equipment, e.g., a sample collection apparatus, a nucleotide amplification apparatus, a nucleotide sequencing apparatus, or a hybridization apparatus. The computer can then collect applicable data gathered by the laboratory device. The data can be stored on a computer at any step, e.g., while collected in real time, prior to the sending, during or in conjunction with the sending, or following the sending. The data can be stored on a computer-readable medium that can be extracted from the computer. The data collected or stored can be transmitted from the computer to a remote location, e.g., via a local network or a wide area network such as the internet.

OTHER EMBODIMENTS

While the invention has been described as providing Bloom filters that identify membership in whole chromosomes, the invention is not so limited. Bloom filters can be constructed to identify members in larger domains such as groups of chromosomes or even whole genomes or collections of genomes. Further, Bloom filters can be constructed to identify members in smaller domains such as chromosome strands, sub-strand regions, or other standard or custom regions.

It should also be understood that Bloom filters are but one implementation of a set membership tester. The invention may be implemented using other set membership testers. Other set membership techniques may test in a more of brute force manner that may be constrained by memory resources in the aligner. In one extreme, the array itself provides one bit for every single possible read. In one implementation, such tester employs a single hash function to define the bit position for each read.

What is claimed is:

1. A method, implemented on a computer system comprising one or more processors and system memory, for detecting copy number variations, the method comprising:
   (a) receiving, by the computer system, a plurality of reads obtained from a sample;
   (b) providing, on the computer system, a plurality of One Read Bloom filters corresponding to a plurality of regions of a genome and a plurality of Multiple Read Bloom filters corresponding to the plurality of regions of the genome, wherein
      each Bloom filter comprises a bit array, one or more hash functions, and logic for applying reads to the Bloom filter,
      each One Read Bloom filter was constructed using approximately read-sized sequences in its corresponding region of the genome, and
      each Multiple Read Bloom filter was constructed using approximately read-sized sequences found more than once in its corresponding region of the genome;

(c) applying, by the one or more processors, each read of the plurality of reads to each One Read Bloom filter to determine a membership of each read in each One Read Bloom filter, wherein applying a read to a Bloom filter comprises:
  providing the read as an input to each hash function of the one or more hash functions of the Bloom filter,
  obtaining an output value from each hash function and the read, wherein each output value is associated with a bit position in the bit array of the Bloom filter, and
  determining that the read is a member of the Bloom filter based on bit values of the bit array at bit positions associated with output values obtained from the one or more hash functions and the read;
(d) applying, by the one or more processors, each read of the plurality of reads to each Multiple Read Bloom filter to determine a membership of each read in each Multiple Read Bloom filter;
(e) determining, based on the memberships determined in (c) and (d) and by the one or more processors, which one or more regions of the plurality of regions the reads are aligned to;
(f) determining, by the one or more processors, from a number of reads aligned to each of the plurality of regions of the genome, read abundance values of the plurality of regions of the genome;
(g) comparing, on a region-to-region basis and by the one or more processors, a read abundance value of each region of the plurality of regions of the genome to a threshold number to produce one or more statistical values indicating aberrations of read abundance in one or more regions of the plurality of regions; and
(h) making, based on the one or more statistical values, one or more detection calls of copy number variation in one or more of the plurality of regions of the genome.

2. The method of claim 1, wherein determining the read abundance values of the plurality of regions comprises excluding a read from any of the plurality of regions when the read is a member of two or more filters of the plurality of One Read Bloom filters.

3. The method of claim 1, wherein the plurality of regions of the genome corresponds to a plurality of chromosomes of an organism, and the copy number variation comprises a chromosomal aneuploidy.

4. The method of claim 1, wherein the sample comprises a mixture of genomes.

5. The method of claim 4, wherein the sample comprises cells taken from a pregnant individual.

6. The method of claim 1, wherein at least one of the Bloom filters comprises 9 or 10 hash functions.

7. The method of claim 6, wherein the hash functions require at most about 5 machine instructions to hash a character.

8. The method of claim 1, wherein at least one of the Bloom filters comprises a bit array having between about $1.5 \times 10^{10}$ to $8.5 \times 10^{11}$ bit positions.

9. The method of claim 1, wherein at least one of the Bloom filters has a false positive probability of at most about 0.00001.

10. The method of claim 1, wherein the plurality of regions of a genome are portions of chromosomes, and the copy number variation comprises a partial chromosomal aneuploidy.

11. The method of claim 1, further comprising applying the plurality of reads to an exclusion region Bloom filter to determine whether any reads should be excluded from alignment to any regions.

12. The method of claim 1, wherein at least one Multiple Read Bloom filter of the plurality of Multiple Read Bloom filters was constructed using repeated sequences.

13. The method of claim 12, wherein the repeated sequences are located in the at least one Multiple Read Bloom filter's corresponding region of the genome.

14. The method of claim 1, wherein at least one filter of the plurality of One Read Bloom filters was constructed using approximately read-sized sequences in its corresponding region of the genome but not in one or more exclusion regions in its corresponding region of the genome.

15. The method of claim 14, wherein at least one Multiple Read Bloom filter of the plurality of Multiple Read Bloom filters was constructed using approximately read-sized sequences in the one or more exclusion regions, as well as approximately read-sized sequences found more than once in its corresponding region of the genome.

16. The method of claim 1, wherein (e) comprises determining a read is aligned to a region when the read is a member of a One Read Bloom filter of the region and is not a member of any of the plurality of Multiple Read Bloom filters.

17. The method of claim 1, wherein (e) comprises determining a read is aligned to a region when the read is a member of a One Read Bloom filter of the region and is not a member of any of the plurality of Multiple Read Bloom filters or any other One Read Bloom filters.

18. The method of claim 1, wherein the plurality of regions of the genome corresponds to a plurality of chromosome strands, sub-strand regions, or custom regions.

19. The method of claim 1, wherein the approximately read-sized sequences fit into one or more read sizes of the plurality of reads.

20. A computer program product for detecting copy number variations, the computer program product comprising a non-transitory computer readable medium on which is provided program instructions comprising:
  (a) code for receiving a plurality of reads obtained from a sample;
  (b) code for providing a plurality of One Read Bloom filters corresponding to a plurality of regions of a genome and a plurality of Multiple Read Bloom filters corresponding to the plurality of regions of the genome, wherein
  each Bloom filter comprises a bit array, one or more hash functions, and logic for applying reads to the Bloom filter,
  each One Read Bloom filter was constructed using approximately read-sized sequences in its corresponding region of the genome, and
  each Multiple Read Bloom filter was constructed using approximately read-sized sequences found more than once in its corresponding region of the genome;
  (c) code for applying each read of the plurality of reads to each One Read Bloom filter to determine a membership of each read in each One Read Bloom filter, wherein applying a read to a Bloom filter comprises:
    providing the read as an input to each hash function of the one or more hash functions of the Bloom filter,
    obtaining an output value from each hash function and the read, wherein each output value is associated with a bit position in the bit array of the Bloom filter, and determining that the read is a member of the Bloom filter based on bit values of the bit array at bit positions associated with output values obtained from the one or more hash functions and the read;

(d) code for applying each read of the plurality of reads to each Multiple Read Bloom filter to determine a membership of each read in each Multiple Read Bloom filter;

(e) code for determining, based on the memberships determined in (c) and (d), which one or more regions of the plurality of regions the reads are aligned to;

(f) code for determining, from a number of reads aligned to each of the plurality of regions of the genome, read abundance values of the plurality of regions of the genome;

(g) code for comparing, on a region-to-region basis, a read abundance value of each region of the plurality of regions of the genome to a threshold number to produce one or more statistical values indicating aberrations of read abundance in one or more regions of the plurality of regions; and (h) code for making, based on the one or more statistical values, one or more detection calls of copy number variation in one or more of the plurality of regions of the genome.

21. An apparatus for aligning nucleic acid sequence reads to a reference sequence, the apparatus comprising:

a sequencer that receives a nucleic acid sample and provides reads of nucleic acid sequences from the nucleic acid sample; and a sequence alignment tool comprising a computer program product comprising a non-transitory computer readable medium on which is provided program instructions comprising:

(a) code for receiving a plurality of reads obtained from a sample;

(b) code for providing a plurality of One Read Bloom filters corresponding to a plurality of regions of a genome and a plurality of Multiple Read Bloom filters corresponding to the plurality of regions of the genome, wherein each Bloom filter comprises a bit array, one or more hash functions, and logic for applying reads to the Bloom filter, each One Read Bloom filter was constructed using approximately read-sized sequences in its corresponding region of the genome, and each Multiple Read Bloom filter was constructed using approximately read-sized sequences found more than once in its corresponding region of the genome;

(c) code for applying each read of the plurality of reads to each One Read Bloom filter to determine a membership of each read in each One Read Bloom filter, wherein applying a read to a Bloom filter comprises:

providing the read as an input to each hash function of the one or more hash functions of the Bloom filter, obtaining an output value from each hash function and the read, wherein each output value is associated with a bit position in the bit array of the Bloom filter, and determining that the read is a member of the Bloom filter based on bit values of the bit array at bit positions associated with output values obtained from the one or more hash functions and the read;

(d) code for applying each read of the plurality of reads to each Multiple Read Bloom filter to determine a membership of each read in each Multiple Read Bloom filter;

(e) code for determining, based on the memberships determined in (c) and (d), which one or more regions of the plurality of regions the reads are aligned to;

(f) code for determining, from a number of reads aligned to each of the plurality of regions of the genome, read abundance values of the plurality of regions of the genome;

(g) code for comparing, on a region-to-region basis, a read abundance value of each region of the plurality of regions of the genome to a threshold number to produce one or more statistical values indicating aberrations of read abundance in one or more regions of the plurality of regions; and (h) code for making, based on the one or more statistical values, one or more detection calls of copy number variation in one or more of the plurality of regions of the genome.

* * * * *

SEQUENCE LISTING

```
<160> NUMBER OF SEQ ID NOS: 2

<210> SEQ ID NO 1
<211> LENGTH: 23
<212> TYPE: DNA
<213> ORGANISM: Artificial Sequence
<220> FEATURE:
<223> OTHER INFORMATION: Synthetic polynucleotide

<400> SEQUENCE: 1
atcgtggtac cctgtggcat atg                                            23

<210> SEQ ID NO 2
<211> LENGTH: 11
<212> TYPE: DNA
<213> ORGANISM: Artificial Sequence
<220> FEATURE:
<223> OTHER INFORMATION: Synthetic polynucleotide

<400> SEQUENCE: 2
atcgtggtaa t                                                         11
```